(12) United States Patent
Liang et al.

(10) Patent No.: US 9,764,005 B2
(45) Date of Patent: *Sep. 19, 2017

(54) SUPPRESSION OF CANCER METASTASIS

(71) Applicant: Academia Sinica, Taipei (TW)

(72) Inventors: Shu-Mei Liang, Bethesda, MD (US); Ching-Feng Chiu, Tainan (TW); Shao-Wen Hung, Pingtung County (TW); Jei-Ming Peng, Taoyuan (TW); Chi-Ming Liang, Bethesda, MD (US)

(73) Assignee: Academia Sinica, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/836,380

(22) Filed: Aug. 26, 2015

(65) Prior Publication Data

US 2016/0051634 A1    Feb. 25, 2016

Related U.S. Application Data

(60) Division of application No. 13/510,753, filed as application No. PCT/US2010/057493 on Nov. 19, 2010, now abandoned, which is a continuation of application No. 12/623,162, filed on Nov. 20, 2009, now Pat. No. 8,357,652.

(60) Provisional application No. 61/281,917, filed on Nov. 23, 2009.

(51) Int. Cl.
| | |
|---|---|
| *A61K 38/38* | (2006.01) |
| *A61K 38/16* | (2006.01) |
| *A61K 47/48* | (2006.01) |
| *C07K 14/765* | (2006.01) |
| *A61K 45/06* | (2006.01) |
| *A61N 5/10* | (2006.01) |
| *C12N 7/00* | (2006.01) |

(52) U.S. Cl.
CPC .......... *A61K 38/385* (2013.01); *A61K 38/162* (2013.01); *A61K 38/38* (2013.01); *A61K 45/06* (2013.01); *A61K 47/48284* (2013.01); *A61N 5/10* (2013.01); *C07K 14/765* (2013.01); *C12N 7/00* (2013.01); *C12N 2770/32133* (2013.01)

(58) Field of Classification Search
None
See application file for complete search history.

(56) References Cited

U.S. PATENT DOCUMENTS

| | | | |
|---|---|---|---|
| 5,922,676 A | 7/1999 | Pasqualini et al. | |
| 6,299,856 B1 | 10/2001 | DeVore et al. | |
| 6,749,868 B1 | 6/2004 | Desai et al. | |
| 2008/0090752 A1 | 4/2008 | Wagner et al. | |
| 2008/0300186 A1* | 12/2008 | Liang ................. | A61K 31/7088 514/17.2 |
| 2009/0214669 A1 | 8/2009 | Bauer et al. | |

FOREIGN PATENT DOCUMENTS

| | | |
|---|---|---|
| EP | 0503829 A2 | 9/1992 |
| WO | WO 2009/114831 | 9/2009 |

OTHER PUBLICATIONS

Friedlander et al, The Oncologist 7:342-347, 2002.*
Gelamo et al, BBA 1594:84-99, 2002, IDS item V, filed on Aug. 26, 2015.*
Cancer.Net publication, Sep. 2015.*
BMC Biothech. 9: Jan. 2, 2009, IDS item 2, filed Nov. 6, 2013.
Gelamo et al Biochim et Biophy acta 1594:84-99, 2002.
Morris PG et al. "Microtubule active agents: beyond the taxane frontier"; Clin Cancer Res., 2008, 14(22), p. 7167-72.
EESR issued Mar. 26, 2013.
Huang et al., "Albumin fibrillization induces apoptosis via integrin/FAK/Akt pathway", BMC Biotechnology, Jan. 8, 2009, pp. 1-12.
International Search Report for corresponding PCT application No. PCT/US2010/057493 mailed Feb. 2, 2011.

* cited by examiner

*Primary Examiner* — Lei Yao
(74) *Attorney, Agent, or Firm* — Cesari and McKenna, LLP

(57) ABSTRACT

Methods of using fibrillar proteins are provided for suppressing cancer metastasis. Cancer metastasis is the most common cause of treatment failure and death in cancer patients. Tumor cell invasion and/or migration can be significantly inhibited after fibrillar proteins (rVP1, F-HSA, and F-BSA) treatment in vitro. In addition, rVP1 can significantly suppress murine and human breast cancer metastasis and human prostate and ovarian cancer metastasis in vivo while F-HSA can significantly suppress murine breast cancer metastasis.

10 Claims, 22 Drawing Sheets

SUPPRESSION OF CANCER METASTASIS

CROSS-REFERENCE TO RELATED APPLICATION

This application claims priority to U.S. patent application Ser. No. 13/510,753 filed Jul. 31, 2012, which is the U.S. National Stage Application of International Application Number PCT/US2010/057493 filed Nov. 19, 2010, which claims the benefit of Provisional Application No. 61/281,917 filed Nov. 23, 2009 and U.S. patent application Ser. No. 12/623,162 filed Nov. 20, 2009, the disclosure of which is incorporated herein by reference.

INTRODUCTION

Cancer metastasis is a process that involves a series of sequential steps and requires a cascade of host-tumor cell interactions (Steeg P S et al. (2007) Nature 449:671-3). These steps include detachment from the primary tumor, invasion into and arrest in circulatory systems, extravasation into the parenchyma of organs; and proliferation in association with angiogenesis (Sawyer T K et al. (2004) Expert Opin Investig Drugs 13:1-19). There are growing interests in investigating the mechanisms of migration and invasion, which are unveiled to be a critical step of the metastatic process. Interference at any one of these steps to block the metastatic cascade represents an attractive approach to prevent the formation of metastatic tumor growths.

Our previous data showed that recombinant capsid protein VP1 (rVP1) of foot-and-mouth disease virus (FMDV), induced apoptosis in several kinds of cancer cells via integrin signaling pathway (Peng J M et al. (2004) J. Biol. Chem. 279:52168-74). It was discovered that using the same process for refolding rVP1 into water-soluble form, globular bovine serum albumin (G-BSA) can be converted into fibrillar BSA (F-BSA), which like rVP1, induced tumor cell apoptosis via integrin/FAK/Akt signaling pathway (Huang et al. (2009) BMC Biotechnol. 9:2).

SUMMARY OF THE INVENTION

Methods are provided for suppressing cancer metastasis. Cancer metastasis is the most common cause of treatment failure and death in cancer patients. Tumor cell invasion and/or migration is significantly inhibited after contacting the tumor cells with fibrillar proteins, which fibrillar proteins include, without limitation, rVP1, F-HSA, and F-BSA. Tumor cells of interest include carcinomas, for example breast carcinoma, epithelial adenocarcinoma of the ovary, adenocarcinoma of the prostate, etc.

In one aspect, the invention relates to a composition comprising a therapeutically effective amount of fibrillar human serum albumin and a pharmaceutically acceptable carrier for use in treating a mammal having cancer, e.g. for suppressing cancer cells, suppressing metastasis, etc.

In some embodiments of the invention, tumor cells are contacted in vivo with fibrillar proteins, which contacting may be local, e.g. intratumoral introduction or injection, or systemic. For example rVP1 is shown herein to significantly suppress murine and human breast cancer metastasis and human prostate and ovarian cancer metastasis in vivo. F-HSA is shown to significantly suppress breast cancer metastasis. In one embodiment, the invention relates to a composition as aforementioned for use in treating cancer in a mammal, wherein the cancer is at least one chosen from breast cancer, ovarian cancer, cervical cancer, prostate cancer, and lung cancer.

In some embodiments of the invention compositions of fibrillar proteins as anti-cancer metastasis therapeutics are provided, where the composition provides for a pharmaceutical formulation in a dose effective to inhibit metastasis. In another aspect, the invention relates to a method comprising manufacturing a composition for use in treating a patient having cancer. The method comprises manufacturing fibrillar human serum albumin, and mixing the fibrillar human serum albumin with a pharmaceutically acceptable carrier. In another aspect, the invention relates to a method comprising dissolving HSA in an SDS solution; applying the dissolved HSA through a gel filtration column with a pore size to separate proteins of 70 kDa molecular weight and above; eluting the HSA from the column; and dialyzing the solution against phosphate buffered saline to remove the SDS.

DEFINITIONS

Figure 1:
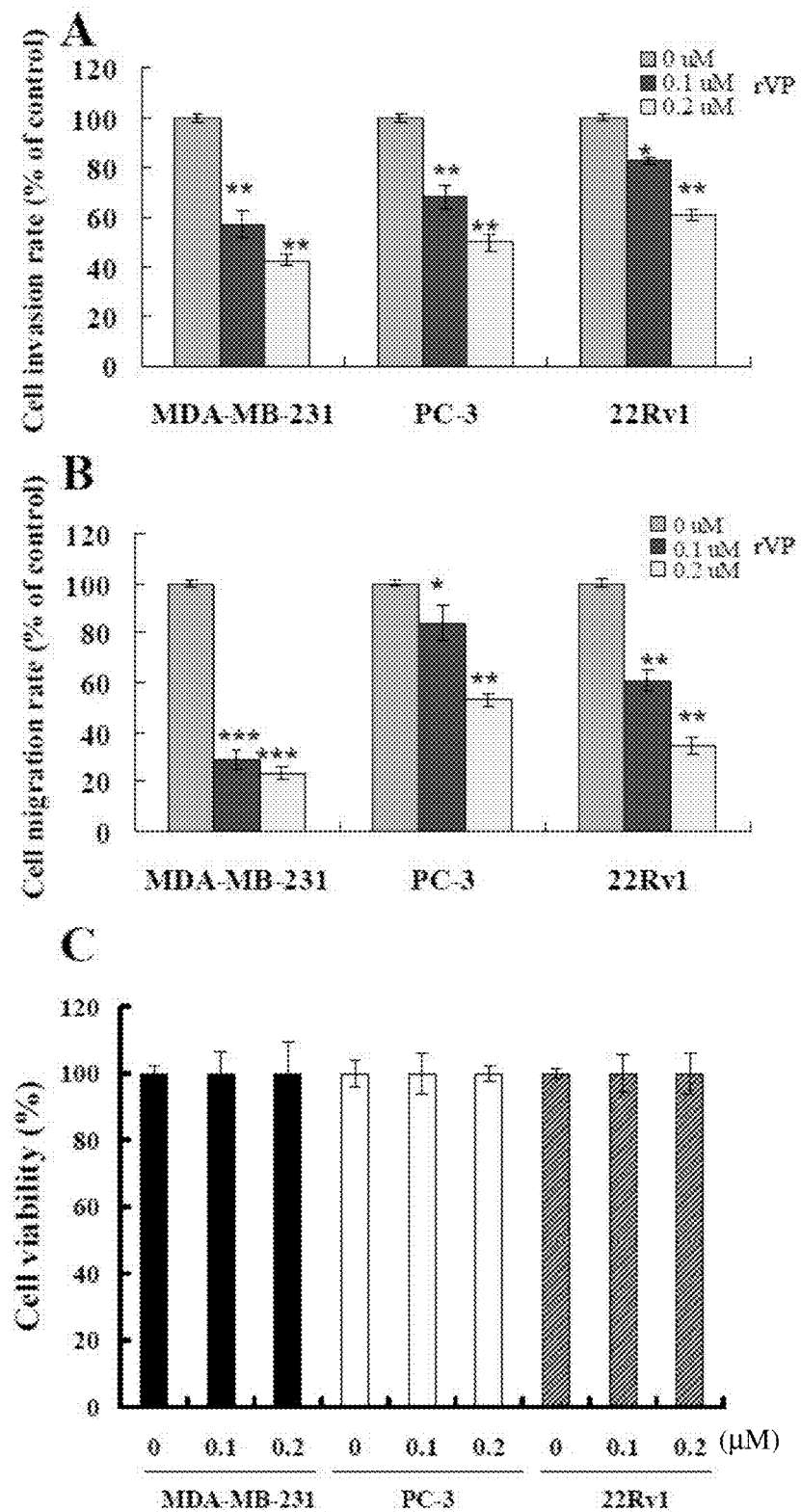
FIG. 1. The effects of rVP1 on cell invasion/migration and cytotoxicity in MDA-MB-231 cells, PC-3 cell, and 22Rv1 cells. (A&B) Cell invasion/migration of MDA-MB-231 cells, PC-3 cell, and 22Rv1 cells with rVP1 treatment for 24 hrs was measured by using Boyden chamber assay. rVP1 significantly suppressed tumor cell invasion/migration (C) The cytotoxicity of MDA-MB-231 cells, PC-3 cell, and 22Rv1 cells with rVP1 treatment for 24 hrs was measured by using MTT assay. 0.1 µM and 0.2 µM rVP1 did not affect tumor cell viability. Data represent means±S.D. (n=3). *: $P<0.05$, : $P<0.01$ and *: $P<0.001$ were relative to control (0 µM rVP1 treatment).

In the description that follows, a number of terms conventionally used in the field of cell culture are utilized extensively. In order to provide a clear and consistent understanding of the specification and claims, and the scope to be given to such terms, the following definitions are provided.

The terms "subject," "individual," and "patient" are used interchangeably herein to refer to a mammal being assessed for treatment and/or being treated. In an embodiment, the mammal is a human. The terms "subject," "individual," and "patient" thus encompass individuals having cancer (e.g., colorectal cancer, adenocarcinoma of the ovary or prostate, breast carcinoma, etc.), including those who have undergone or are candidates for resection (surgery) to remove cancerous tissue (e.g., cancerous colorectal tissue). Subjects may be human, but also include other mammals, particularly those mammals useful as laboratory models for human disease, e.g. mouse, rat, etc.

As used herein, the terms "treatment," "treating," and the like, refer to administering an agent, or carrying out a procedure (e.g., radiation, a surgical procedure, etc.), for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, covers any treatment of any metastatic tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. In tumor (e.g., cancer) treatment, a therapeutic agent may directly decrease the metastasis of tumor cells.

The term "cell culture" or "culture" means the maintenance of cells in an artificial, in vitro environment. It is to be understood, however, that the term "cell culture" is a generic term and may be used to encompass the cultivation not only of individual cells, but also of tissues or organs.

The term "tumor," as used herein, refers to all neoplastic cell growth and proliferation, whether malignant or benign, and all pre-cancerous and cancerous cells and tissues.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. In general, cells of interest for detection, analysis, classification, or treatment in the present application include precancerous (e.g., benign), malignant, pre-metastatic, metastatic, and non-metastatic cells. Examples of cancer include but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

Depending on the nature of the cancer, an appropriate patient sample is obtained. As used herein, the phrase "cancerous tissue sample" refers to any cells obtained from a cancerous tumor. In the case of solid tumors which have not metastasized, a tissue sample from the surgically removed tumor will typically be obtained and prepared for testing by conventional techniques. Alternatively, a body fluid sample, such as lymph, blood or serum sample, or an exudate fluid sample such as the cancerous organ exudate (e.g., exudate from the breast) may be collected and used as the sample to be analyzed. In the case of leukemias, lymphocytes or leukemic cells will be obtained and appropriately prepared. Similarly, in the case of any metastasized cancer, cells may be drawn from a body fluid such as lymphatic fluid, blood, serum, or a distally infected organ or exudate thereof.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body. Therefore, the present invention contemplates a method of determining the risk of further growth of one or more cancerous tumors in an organ or body part which is not directly connected to the organ of the original cancerous tumor and/or any steps in a process leading up to that growth.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as lung, colon, skin or esophageal cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the phrase "disease-free survival," refers to the lack of such tumor recurrence and/or spread and the fate of a patient after diagnosis, with respect to the effects of the cancer on the life-span of the patient. The phrase "overall survival" refers to the fate of the patient after diagnosis, despite the possibility that the cause of death in a patient is not directly due to the effects of the cancer. The phrases, "likelihood of disease-free survival", "risk of recurrence" and variants thereof, refer to the probability of tumor recurrence or spread in a patient subsequent to diagnosis of cancer, wherein the probability is determined according to the process of the invention.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

The term "isolated" is intended to mean that a compound is separated from all or some of the components that accompany it in nature. "Isolated" also refers to the state of a compound (e.g. protein) separated from all or some of the components that accompany it during manufacture (e.g., chemical synthesis, recombinant expression, culture medium, and the like).

A "biological sample" encompasses a variety of sample types obtained from an individual. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

DESCRIPTION OF THE SPECIFIC EMBODIMENTS

The present disclosure relates to a process of producing fibrillar proteins and methods of treatment using fibrillar proteins. The method of treatment involves suppression of cancer metastasis.

Method of Treatment

A method is disclosed herein for inhibiting cancer metastasis. The method involves administering a therapeutically effective amount of the fibrillar structure protein to a patient in need thereof. The method can further involve the steps of providing a protein, and changing the protein into a fibrillar structure prior to administering the fibrillar protein. Administration of the fibrillar protein inhibits tumor cell invasion (e.g. into surrounding tissues) and/or migration.

The present method finds use in a variety of cancer therapies (including cancer prevention and post-diagnosis cancer therapy) in a mammalian subject, particularly in a human. Subjects having, suspected of having, or at risk of developing a tumor are contemplated for therapy described herein.

Anti-cancer therapies in accordance with the subject method can be particularly directed to cancerous cells that are metastatic or at a high risk of becoming metastatic. As such, fibrillar protein can be used therapeutically to effect/prevent adhesion and invasion of cancer cells in other tissues.

For example, the cancer metastases that can be inhibited by the method of the present disclosure include, but are not limited to, carcinomas, including adenocarcinomas, and particularly breast carcinomas, adenocarcinoma of the prostate and adenocarcinoma of the ovary. Other metastases that can be treated include those that originate from cancerous growth in kidney, lung, liver, skin (e.g. melanoma), colon, pancreas, or cervix.

The fibrillar structure protein used to treat the cancer can be an albumin, fibronectin, rVP1, rVP2, rVP3, P1, or chimeric protein comprising parts from VP1, VP2, VP3, and/or VP4. Albumin proteins may be obtained from any animal of interest, e.g. human serum albumin, bovine serum albumin, etc. In certain embodiments, the fibrillar protein additionally induces cancer cell apoptosis by modulating the Akt signaling pathway. In some instances, the fibrillar protein modulates integrin $\alpha5\beta1$ or $\alpha v\beta3$ which leads to the deactivation of Akt. In other instances, fibrillar albumin binds to integrin and causes cellular apoptosis mainly through the integrin/FAK/Akt/GSK-3$\beta$/caspase-3 pathway.

As noted above, the present method involves administering fibrillar proteins to a subject (e.g. a human patient) to, for example, to suppress invasion and migration of cancerous cells. This can be accomplished by administering a fibrillar protein to the subject as described herein so as to provide for a decrease in the metastasis of a cancer as compared to subjects who are not administered the fibrillar protein. Therapies in accordance with the subject methods can also be useful in preventing relapse, reducing migration of cancer cells, reducing tumor size, reducing tumor load, and/or improving the clinical outcome in patients.

Types of Cancer

The methods relating to cancer contemplated herein include, for example, use of fibrillar protein therapy as an anti-cancer metastasis therapy. The methods are useful in the context of treating or preventing a wide variety of cancers, such as cancers that can metastasize (e.g. carcinomas and sarcomas).

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelieal carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be amenable to therapy by a method disclosed herein include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Other cancers that can be amenable to treatment according to the methods disclosed herein include atypical meningioma (brain), islet cell carcinoma (pancreas), medullary carcinoma (thyroid), mesenchymoma (intestine), hepatocellular carcinoma (liver), hepatoblastoma (liver), clear cell carcinoma (kidney), and neurofibroma mediastinum.

Further exemplary cancers that can be amenable to treatment using a methods disclosed herein include, but are not limited to, cancers of neuroectodermal and epithelial origin. Examples of cancers of neuroectodermal origin include, but are not limited to, Ewings sarcoma, spinal tumors, brain tumors, supratenbrial primative neuroectodermal tumors of infancy, tubulocystic carcinoma, mucinous tubular and spindle cell carcinoma, renal tumors, mediastinum tumors, neurogliomas, neuroblastomas, and sarcomas in adolescents and young adults. Examples of epithelial origin include, but are not limited to, small cell lung cancer, cancers of the breast, eye lens, colon, pancreas, kidney, liver, ovary, and bronchial epithelium.

Combinations with Other Cancer Therapies

Therapeutic administration of the fibrillar protein can include administration as a part of a therapeutic regimen that may or may not be in conjunction with additional standard anti-cancer therapeutics, including but not limited to immunotherapy, chemotherapeutic agents and surgery (e.g., as those described further below).

In addition, therapeutic administration of the fibrillar protein can also be post-therapeutic treatment of the subject with an anti-cancer therapy, where the anti-cancer therapy can be, for example, surgery, radiation therapy, administration of chemotherapeutic agents, and the like. Cancer therapy using fibrillar proteins of the present disclosure can also be used in combination with immunotherapy. In other examples, the fibrillar proteins can be administered in combination with one or more chemotherapeutic agents (e.g., cyclophosphamide, doxorubicin, vincristine and prednisone (CHOP)), and/or in combination with radiation treatment and/or in combination with surgical intervention (e.g., pre- or post-surgery to remove a tumor). Where the fibrillar proteins are used in connection with surgical intervention, the fibrillar protein can be administered prior to, at the time of, or after surgery to remove cancerous cells, and may be administered systemically or locally at the surgical site. The fibrillar protein alone or in combinations described above can be administered systemically (e.g., by parenteral administration, e.g., by an intravenous route) or locally (e.g., at a local tumor site, e.g., by intratumoral administration (e.g., into a solid tumor, into an involved lymph node in a lymphoma or leukemia), administration into a blood vessel supplying a solid tumor, etc.).

Any of a wide variety of cancer therapies can be used in combination with the fibrillar protein therapies described herein. Such cancer therapies include surgery (e.g., surgical removal of cancerous tissue), radiation therapy, bone marrow transplantation, chemotherapeutic treatment, biological response modifier treatment, and certain combinations of the foregoing.

Radiation therapy includes, but is not limited to, X-rays or gamma rays that are delivered from either an externally applied source such as a beam, or by implantation of small radioactive sources.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (CYTOXAN™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (TAXOL®), docetaxel (TAXOTERE®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (TAXOL®), TAXOL® derivatives, docetaxel (TAXOTERE®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and ZOLADEX®. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); IRESSA® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL, TAXOTERE (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art.

Paclitaxel should be understood to refer to not only the common chemically available form of paclitaxel, but analogs and derivatives (e.g., TAXOTERE™ docetaxel, as noted above) and paclitaxel conjugates (e.g., paclitaxel-PEG, paclitaxel-dextran, or paclitaxel-xylose).

In the treatment of some individuals in accordance with the method of the present disclosure, it may be desirable to use a high dose regimen in conjunction with a rescue agent for non-malignant cells. In such treatment, any agent capable of rescue of non-malignant cells can be employed, such as citrovorum factor, folate derivatives, or leucovorin. Such rescue agents are well known to those of ordinary skill in the art. Rescue agents include those which do not interfere with the ability of the present inventive compounds to modulate cellular function.

Administration of the Fibrillar Protein

Administration of the fibrillar protein may be achieved through various methods to different parts of the body, including intratumoral, intravenous, intradermal, subcutaneous, oral (e.g., inhalation), transdermal (i.e., topical), transmucosal, intraperitoneal, intraarterial, and rectal administration. Other suitable routes include administration of the composition orally, bucally, nasally, nasopharyngeally, parenterally, enterically, gastrically, topically, transdermally, subcutaneously, intramuscularly, in tablet, solid, powdered, liquid, aerosol form, intralesional injection into the tumor, intralesional injection adjacent to the tumor, intravenous infusion, and intraarterial infusion. Administration may be done locally or systemically, with or without added excipients. Administering can also be done via slow release mode at or around tumor sites of a subject.

One skilled in the art will appreciate that a variety of suitable methods of administering a formulation of the present disclosure to a subject or host, e.g., patient, in need thereof, are available, and, although more than one route can be used to administer a particular formulation, a particular route can provide a more immediate and more effective reaction than another route.

The phrase "therapeutically effective amount" refers to an amount that produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

According to exemplary implementations, the protein may be administered as part of a composition, which is described in more detail below. The composition may be in various forms including powders, creams, gels, salves, ointments, solutions, tablets, capsules, sprays, and patches. Vehicles and carriers may be used for delivery of the composition to the patient. Such carriers include solubilizing agents, diluents, and dispersion media. These carriers are biocompatible, pharmaceutically acceptable, and do not alter the treatment characteristics of the fibrillar protein. Excipients, adjuvants and other ingredients may also be included in the composition.

Dosage

In the methods, an effective amount of a fibrillar protein is administered to a subject in need thereof. In particular, fibrillar proteins of specific interest are those that inhibit metastasis of a cancer in a host when the fibrillar proteins are administered in an effective amount. The amount administered varies depending upon the goal of the administration, the health and physical condition of the individual to be treated, age, the taxonomic group of individual to be treated (e.g., human, non-human primate, primate, etc.), the degree of resolution desired, the formulation of the fibrillar protein composition, the treating clinician's assessment of the medical situation, and other relevant factors. It is expected that the amount will fall in a relatively broad range that can be determined through routine trials. For example, the amount of fibrillar protein employed to inhibit cancer metastasis is not more than about the amount that could otherwise be irreversibly toxic to the subject (i.e., maximum tolerated dose). In other cases the amount is around or even well below the toxic threshold, but still in an immunoeffective concentration range, or even as low as threshold dose.

Individual doses are typically not less than an amount required to produce a measurable effect on the subject, and may be determined based on the pharmacokinetics and pharmacology for absorption, distribution, metabolism, and excretion ("ADME") of the fibrillar protein of its by-products, and thus based on the disposition of the composition within the subject. This includes consideration of the route of administration as well as dosage amount, which can be adjusted for topical (applied directly where action is desired for mainly a local effect), enteral (applied via digestive tract for systemic or local effects when retained in part of the digestive tract), or parenteral (applied by routes other than the digestive tract for systemic or local effects) applications. For instance, administration of the fibrillar protein is typically via injection and often intravenous, intramuscular, intratumoral, or a combination thereof.

The fibrillar protein may be administered by infusion or by local injection, e.g. by infusion at a rate of about 50 mg/h to about 400 mg/h, including about 75 mg/h to about 375 mg/h, about 100 mg/h to about 350 mg/h, about 150 mg/h to about 350 mg/h, about 200 mg/h to about 300 mg/h, about 225 mg/h to about 275 mg/h. Exemplary rates of infusion can achieve a desired therapeutic dose of, for example, about 0.5 mg/m$^2$/day to about 10 mg/m$^2$/day, including about 1 mg/m$^2$/day to about 9 mg/m$^2$/day, about 2 mg/m$^2$/day to about 8 mg/m$^2$/day, about 3 mg/m$^2$/day to about 7 mg/m$^2$/day, about 4 mg/m$^2$/day to about 6 mg/m$^2$/day, about 4.5 mg/m$^2$/day to about 5.5 mg/m$^2$/day. Administration (e.g, by infusion) can be repeated over a desired period, e.g., repeated over a period of about 1 day to about 5 days or once every several days, for example, about five days, over about 1 month, about 2 months, etc. It also can be administered prior, at the time of, or after other therapeutic interventions, such as surgical intervention to remove cancerous cells. The fibrillar protein can also be administered as part of a combination therapy, in which at least one of an immunotherapy, a cancer chemotherapy or a radiation therapy is administered to the subject (as described in greater detail below).

Disposition of the fibrillar protein and its corresponding biological activity within a subject is typically gauged against the fraction of fibrillar protein present at a target of interest. For example, a fibrillar protein once administered can accumulate with a glycoconjugate or other biological target that concentrates the material in cancer cells and cancerous tissue. Thus dosing regimens in which the fibrillar protein is administered so as to accumulate in a target of interest over time can be part of a strategy to allow for lower individual doses. This can also mean that, for example, the dose of fibrillar protein that are cleared more slowly in vivo can be lowered relative to the effective concentration calculated from in vitro assays (e.g., effective amount in vitro approximates mM concentration, versus less than mM concentrations in vivo).

As an example, the effective amount of a dose or dosing regimen can be gauged from the IC$_{50}$ of a given fibrillar protein for inhibiting cell migration. By "IC$_{50}$" is intended the concentration of a drug required for 50% inhibition in vitro. Alternatively, the effective amount can be gauged from the EC$_{50}$ of a given fibrillar protein concentration. By "EC$_{50}$" is intended the plasma concentration required for obtaining 50% of a maximum effect in vivo. In related embodiments, dosage may also be determined based on ED$_{50}$ (effective dosage).

In general, with respect to the fibrillar protein of the present disclosure, an effective amount is usually not more than 200× the calculated IC$_{50}$. Typically, the amount of an fibrillar protein that is administered is less than about 200×, less than about 150×, less then about 100× and many embodiments less than about 75×, less than about 60×, 50×, 45×, 40×, 35×, 30×, 25×, 20×, 15×, 10× and even less than about 8× or 2× than the calculated IC$_{50}$. In one embodiment, the effective amount is about 1× to 50× of the calculated IC$_{50}$, and sometimes about 2× to 40×, about 3× to 30× or about 4× to 20× of the calculated IC$_{50}$. In other embodiments, the effective amount is the same as the calculated IC$_{50}$, and in certain embodiments the effective amount is an amount that is more than the calculated IC$_{50}$.

An effect amount may not be more than 100× the calculated $EC_{50}$. For instance, the amount of fibrillar protein that is administered is less than about 100×, less than about 50×, less than about 40×, 35×, 30×, or 25× and many embodiments less than about 20×, less than about 15× and even less than about 10×, 9×, 9×, 7×, 6×, 5×, 4×, 3×, 2× or 1× than the calculated $EC_{50}$. The effective amount may be about 1× to 30× of the calculated $EC_{50}$, and sometimes about 1× to 20×, or about 1× to 10× of the calculated $EC_{50}$. The effective amount may also be the same as the calculated $EC_{50}$ or more than the calculated $EC_{50}$. The $IC_{50}$ can be calculated by inhibiting cell migration/invasion in vitro. The procedure can be carry out by methods known in the art or as described in the examples below.

Effective amounts of dose and/or dose regimen can readily be determined empirically from assays, from safety and escalation and dose range trials, individual clinician-patient relationships, as well as in vitro and in vivo assays such as those described herein and illustrated in the Experimental section, below. For example, a concentration used for carrying out the subject method in mice ranges from about 1 mg/kg to about 25 mg/kg based on the body weight of the mice. Based on this data, an example of a concentration of the fibrillar protein that can be employed in human may range about 0.083 mg/kg to about 2.08 mg/kg. Other dosage may be determined from experiments with animal models using methods known in the art (Reagan-Shaw et al. (2007) *The FASEB Journal* 22:659-661).

Pharmaceutical Formulations

Also provided are pharmaceutical compositions containing the fibrillar protein employed in the methods of treatment described above. The term "fibrillar protein composition" is used herein as a matter of convenience to refer generically to compositions comprising a fibrillar protein of the present disclosure, including conjugated fibrillar protein, or both. Compositions useful for suppression the growth and/or metastasis of cancer cells are described below.

The fibrillar protein compositions, e.g., in the form of a pharmaceutically acceptable salt, can be formulated for oral, topical or parenteral administration, as described above. In certain embodiments, e.g., where a fibrillar protein is administered as a liquid injectable (such as in those embodiments where they are administered intravenously or directly into a tissue), an fibrillar protein formulation is provided as a ready-to-use dosage form, or as a reconstitutable storage-stable powder or liquid composed of pharmaceutically acceptable carriers and excipients.

Methods for producing fibrillar protein suitable for administration to a subject (e.g., a human subject) are described below and also in US Pat Pub No. 2008/0300186, disclosure of which is incorporated by reference. An example method of formulating fibrillar protein can involve a pharmaceutical composition containing an effective amount of a fibrillar protein and a pharmaceutical excipients (e.g., saline). The pharmaceutical composition may optionally include other additives (e.g., buffers, stabilizers, preservatives, and the like). An effective amount of fibrillar protein can be an amount effective to provide for a decrease of cancer metastasis (e.g. cancer migration and/or invasion). A therapeutic goal (e.g., reduction in tumor load and/or confinement of cancerous growth) can be accomplished by single or multiple doses under varying dosing regimen.

The concentration of fibrillar protein in the pharmaceutical formulations can vary from less than about 0.1%, usually at or at least about 2% to as much as 20% to 50% or more by weight, and will be selected primarily by fluid volumes, viscosities, etc., in accordance with the particular mode of administration selected and the patient's needs. The resulting compositions may be in the form of a solution, suspension, tablet, pill, capsule, powder, gel, cream, lotion, ointment, aerosol or the like. Actual methods for preparing parenterally administrable compositions will be known or apparent to those skilled in the art and are described in more detail in such publications as Remington's Pharmaceutical Science, 18th ed., Mack Publishing Company, NY (1995).

According to another aspect of this disclosure, fibrillar HSA can be included in a pharmaceutical or nutraceutical composition together with additional active agents, carriers, vehicles, excipients, or auxiliary agents identifiable by a person skilled in the art upon reading of the present disclosure.

The pharmaceutical or nutraceutical compositions preferably comprise at least one pharmaceutically acceptable carrier. In such pharmaceutical compositions, the fibrillar HSA or fibrillar HSA equivalent forms the "active compound," also referred to as the "active agent." As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for an injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor® EL (BASF, Parsippany, N.J.), or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. According to embodiments, isotonic agents, for example, sugars, polyalcohols such as manitol, sorbitol, or sodium chloride in the composition are added. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preparation is prepared by vacuum drying or freeze-drying, which yields a powder of the active ingredient plus any additional desired ingredient from a previously sterile-filtered solution thereof.

It is recognized that when administered orally, fibrillar protein should be protected from digestion. This is typically accomplished either by complexing the fibrillar protein with a composition to render it resistant to acidic and enzymatic hydrolysis or by packaging in an appropriately resistant carrier such as a liposome. Means of protecting a compound of interest from digestion are well known in the art.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or strawberry, cherry, grape, lemon, or orange flavoring.

For administration by inhalation, the compounds are delivered in the form of an aerosol spray from pressured container or dispenser which contains a suitable propellant, e.g., a gas such as carbon dioxide, or a nebulizer.

In order to enhance serum half-life, fibrillar protein preparations that are injected may also be encapsulated, introduced into the lumen of liposomes, prepared as a colloid, PEGylated (Greenwald et al. (2003) *Advanced Drug Delivery Rev.* 55:217-250; Pasut et al. (2004) Expert Opin. Ther. Patents 14:859-894) or other conventional techniques may be employed which provide an extended serum half-life. A variety of methods are available for preparing liposomes, as described in, e.g., Szoka et al. (1980) *Ann. Rev. Biophys. Bioeng.* 9:467, U.S. Pat. Nos. 4,235,871, 4,501,728 and 4,837,028. The preparations may also be provided in controlled release or slow-release forms for release and administration of the fibrillar protein compositions as a mixture or in serial fashion.

According to embodiments, intravitreal injection is accomplished using PLGA-based microparticles or nanoparticles (liposomes). PEG-based formulas may also be used. Accordingly, the other methods for injectable pharmaceutical compositions are expressly contemplated for intravitreal injection.

Systemic administration can also be transmucosal or transdermal. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In addition to the other forms of delivery, the compounds are deliverable via eye drop or intraocular injection. With respect to eye drops, the compositions of the present disclosure optionally comprise one or more excipients intended for topical application to the eye or nose. Excipients commonly used in pharmaceutical compositions intended for topical application to the eyes, such as solutions or sprays, include, but are not limited to, tonicity agents, preservatives, chelating agents, buffering agents, surfactants and antioxidants. Suitable tonicity-adjusting agents include mannitol, sodium chloride, glycerin, sorbitol and the like. Suitable preservatives include p-hydroxybenzoic acid ester, benzalkonium chloride, benzododecinium bromide, polyquaternium-1 and the like. Suitable chelating agents include sodium edetate and the like. Suitable buffering agents include phosphates, borates, citrates, acetates and the like. Suitable surfactants include ionic and nonionic surfactants, though nonionic surfactants are preferred, such as polysorbates, polyethoxylated castor oil derivatives and oxyethylated tertiary octylphenol formaldehyde polymer (tyloxapol). Suitable antioxidants include sulfites, ascorbates, BHA and BHT. The compositions of the present disclosure optionally comprise an additional active agent. With the exception of the optional preservative ingredient (e.g., polyquaternium-1), the compositions of the present disclosure preferably do not contain any polymeric ingredient other than polyvinylpyrrolidone or polystyrene sulfonic acid.

When the compositions of the present disclosure contain polyvinylpyrrolidone, the polyvinylpyrrolidone ingredient is preferably selected or processed to minimize peroxide content. Freshly produced batches of polyvinylpyrrolidone are preferred over aged batches. Additionally, particularly in cases where the composition will contain greater than 0.5% polyvinylpyrrolidone, the polyvinylpyrrolidone ingredient should be thermally treated (i.e., heated to a temperature above room temperature) prior to mixing with olopatadine in order to reduce the amount of peroxides in the polyvinylpyrrolidone ingredient and minimize the effect of peroxides on the chemical stability of olopatadine. While thermally treating an aqueous solution of polyvinylpyrrolidone for prolonged periods will substantially reduce the amount of peroxides, it can lead to discoloration (yellow to yellowish-brown) of the polyvinylpyrrolidone solution. In order to substantially reduce or eliminate peroxides without discoloring the polyvinylpyrrolidone solution, the pH of the aqueous solution of polyvinylpyrrolidone should be adjusted to pH 11-13 before it is subjected to heat. Much shorter heating times are needed to achieve significant reductions in peroxide levels if the pH of the polyvinylpyrrolidone solution is elevated.

One suitable method of thermally treating the polyvinylpyrrolidone ingredient is as follows. First, dissolve the polyvinylpyrrolidone ingredient in purified water to make a 4-6% solution, then raise the pH of the solution to pH 11-13, (an effective range of pH is 11-11.5), then heat to a temperature in the range of 60-121° C., preferably 65-80° C. and most preferably 70-75° C. The elevated temperature should be maintained for approximately 30-120 minutes (preferably 30 minutes). After the heated solution cools to room temperature, add HCl to adjust the pH to 3.5-8, depending upon the target pH for the olopatadine composition.

Particularly for compositions intended to be administered as eye drops, the compositions preferably contain a tonicity-adjusting agent in an amount sufficient to cause the final composition to have an ophthalmically acceptable osmolality (generally 150-450 mOsm, preferably 250-350 mOsm). The ophthalmic compositions of the present disclosure preferably have a pH of 4-8, preferably a pH of 6.5-7.5, and most preferably a pH of 6.8-7.2.

The eye-drop compositions of the present disclosure are preferably packaged in opaque plastic containers. A preferred container for an ophthalmic product is a low-density polyethylene container that has been sterilized using ethylene oxide instead of gamma-irradiation.

With respect to ophthalmic injectables, the pharmaceutical compositions of this disclosure are administered to the area in need of treatment by subconjunctival administration. One preferred method of subconjunctival administration to the eye is by injectable formulations comprising the pharmaceutical compositions disclosed herein. Another preferred method of subconjunctival administration is by implantations comprising slow releasing compositions.

Compositions that are delivered subconjunctivally comprise, according to embodiments, an ophthalmic depot formulation comprising an active agent for subconjunctival administration. According to embodiments, the ophthalmic depot formulation comprises microparticles of essentially pure active agent. The microparticles comprising can be embedded in a biocompatible pharmaceutically acceptable polymer or a lipid encapsulating agent. The depot formulations may be adapted to release all of substantially all the active material over an extended period of time. The polymer or lipid matrix, if present, may be adapted to degrade sufficiently to be transported from the site of administration after release of all or substantially all the active agent. The depot formulation can be liquid formulation, comprising a pharmaceutical acceptable polymer and a dissolved or dispersed active agent. Upon injection, the polymer forms a depot at the injections site, e.g., by gelifying or precipitating.

Solid articles suitable for implantation in the eye can also be designed in such a fashion to comprise polymers and can be bioerodible or non-bioerodible. Bioerodible polymers that can be used in preparation of ocular implants carrying the compositions of the present disclosure include without restriction aliphatic polyesters such as polymers and copolymers of poly(glycolide), poly(lactide), poly(ε-caprolactone), poly(hydroxybutyrate) and poly(hydroxyvalerate), polyamino acids, polyorthoesters, polyanhydrides, aliphatic polycarbonates and polyether lactones. Illustrative of suitable non-bioerodible polymers are silicone elastomers.

According to embodiments, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to cell-specific antigens) can also be used as pharmaceutically acceptable carriers.

The fibrillar protein composition can be administered as a single pharmaceutical formulation. It may also be administered with an effective amount of another agent that includes other suitable compounds and carriers, and also may be used in combination with other active agents. The present disclosure, therefore, also includes pharmaceutical compositions comprising pharmaceutically acceptable excipients.

The pharmaceutically acceptable excipients include, for example, any suitable vehicles, adjuvants, carriers or diluents, and are readily available to the public. The pharmaceutical compositions of the present disclosure may further contain other active agents as are well known in the art. Pharmaceutically acceptable excipients are also well-known to those who are skilled in the art, and are readily available.

For example, the fibrillar protein compositions can be admixed with conventional pharmaceutically acceptable carriers and excipients (i.e., vehicles) and used in the form of aqueous solutions, tablets, capsules, elixirs, suspensions, syrups, wafers, patches and the like, but usually the fibrillar protein will be provided as an injectable. The pharmaceutical compositions may contain common carriers and excipients, such as corn starch or gelatin, lactose, dextrose, sucrose, microcrystalline cellulose, kaolin, mannitol, dicalcium phosphate, sodium chloride, and alginic acid. Disintegrators commonly used in formulations include croscarmellose, microcrystalline cellulose, corn starch, sodium starch glycolate and alginic acid. Preservatives and the like may also be included. Each of these components is well-known in the art. Such pharmaceutical compositions contain, in certain embodiments, from about 0.1 to about 90% by weight of the active compound, and more generally from about 1 to about 30% by weight of the active compound. See, e.g., U.S. Pat. No. 5,985,310, the disclosure of which is herein incorporated by reference The fibrillar protein compositions can be provided in a pharmaceutically acceptable excipient, which can be a solution such as an aqueous solution, often a saline solution, or they can be provided in powder form. The fibrillar protein compositions may contain other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting.

A liquid composition will generally be composed of a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The fibrillar proteins of the present disclosure and their pharmaceutically acceptable salts that are active when given parenterally can be formulated for intramuscular, intrathecal, or intravenous administration. A typical composition for intramuscular or intrathecal administration will be of a suspension or solution of active ingredient in an oil, for example, arachis oil or sesame oil. A typical composition for intravenous or intrathecal administration will be a sterile isotonic aqueous solution containing, for example, active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol, a chelating agent, for example, ethylenediamine tetraacetic acid, and an anti-oxidant, for example, sodium metabisulphite may be included in the formulation. Alternatively, the solution can be freeze dried and then reconstituted with a suitable solvent just prior to administration.

The fibrillar proteins of the present disclosure and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

The fibrillar proteins of the present disclosure and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. No. 5,023,252, herein incorporated by reference in its entirety. Such patches may be constructed for continuous, pulsatile, or on demand delivery of pharmaceutical agents.

The formulations of the present disclosure can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

Formulations suitable for topical administration may be presented as creams, gels, pastes, or foams, containing, in addition to the active ingredient, such carriers as are known in the art to be appropriate.

Suppository formulations are also provided by mixing with a variety of bases such as emulsifying bases or water-soluble bases. Formulations suitable for vaginal administration may be presented as pessaries, tampons, creams, gels, pastes, foams.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more fibrillar protein. Similarly, unit dosage forms for injection or intravenous administration may comprise the fibrillar protein (s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms of the present disclosure depend on the particular compound employed and the effect to be achieved, and the pharmacodynamics associated with each compound in the host.

Those of skill in the art will readily appreciate that dose levels can vary as a function of the specific fibrillar protein, the nature of the delivery vehicle, and the like. Suitable dosages for a given compound are readily determinable by those of skill in the art by a variety of means.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The term "effective amount" refers to an amount of a biologically active molecule or conjugate or derivative thereof sufficient to exhibit a detectable therapeutic effect without undue adverse side effects (such as toxicity, irritation and allergic response) commensurate with a reasonable benefit/risk ratio when used in the manner of the invention. The therapeutic effect may include, for example but not by way of limitation, being substantially cytotoxic to cancer cells, but less cytotoxic to natural cells. The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

Methods of Making Fibrillar Protein

According to the present disclosure, a method is disclosed for treating cancer metastasis by administering a fibrillar protein. The fibrillar protein can be naturally-occurring and as such, can isolated using methods known in the art for use in the method of treatment described above. The fibrillar protein can also be made artificially by any method known in the art, e.g. by changing a globular protein structure into a fibrillar protein structure. In one example, fibrillization of proteins can be induced by a process without the assistance of fibril seed, as disclosed in US Pat Pub No. 2008/0800186, disclosure of which is incorporated herein by reference. This process has advantages which include ease of control, homogeneity of production, and feasibility of scaling up. Moreover, fibrillization of proteins can be induced by this process without the assistance of fibril seed. Even a tiny amount of protein would be applicable to this process. As used herein, "protein" includes one or more proteins, protein fragments, polypeptides, or peptides. Proteins include both synthetic and naturally occurring proteins.

In accordance with the method disclosed previously in US Pat Pub No. 2008/0800186, even a tiny amount of protein would be applicable to this process. As used herein, "protein" includes one or more proteins, protein fragments, polypeptides or peptides. Proteins include both synthetic and naturally occurring proteins. The method can be used to convert native proteins, regardless of their sequence, into fibrillar form in a simple and rapid manner. The method comprises the steps of dissolving a globular protein in a solution that contains detergents and applying the solution to a molecular sizing column that can separate proteins of 70 kDa molecular weight or larger, and eluting the protein with a solution containing detergent. In an exemplary implementation, the method comprises the steps of providing a globular protein, forming a solution containing the globular protein, adding a detergent to the solution containing the globular protein, and applying the solution to a molecular sizing column with a pore size that can separate proteins of 70 kDa molecular weight and above, optionally in the presence of low concentration of detergent.

Globular proteins, also known as spheroproteins, are one of two main tertiary structure classes of proteins. Globular proteins are generally soluble and form speriodal molecules in water. They have a complex secondary structure comprising a mixture of secondary structure motifs, such as α-helices, β-sheets, and loop structures. The other main tertiary structure class of proteins are fibrillar proteins, or fibrous proteins. Fibrillar proteins are generally insoluble and have an elongated shape. They have a simpler secondary structure and are often based on only one type of secondary structure motif. In examples of implementations, the globular protein is an albumin, for example human serum albumin, fibronectin, etc. Recombinant unfolded proteins extracted from the inclusion bodies of E. coli with 8M urea can also be used, for example recombinant caspid protein VP1 of the foot-and-mouth-disease virus (rVP1), recombinant caspid protein VP2 of the foot-and-mouth-disease virus (rVP2), recombinant caspid protein VP3 of the foot-and-mouth-disease virus (rVP3), or precursor protein P1 of VP1, VP2, VP3, and VP4. The protein may also be a chimeric protein comprising parts from VP1, VP2, VP3, and/or VP4, for example VP42, which comprises parts of both VP2 and VP4. Other globular proteins (e.g. bovine serum albumin) may also be used, including both naturally-occurring proteins and synthetic oligopeptides.

Surfactants, also referred to herein as detergents, are substances that lower the surface tension of water and increase the solubility of organic compounds. Detergents may be ionic, which includes cationic, anionic, and zwitterionic detergents, as well as non-ionic. Detergents play a role in disrupting non-covalent bonds in proteins, thereby denaturing the proteins such that they lose their native shape or conformation. In exemplary implementations, the detergent used is sodium dodecyl sulfate (SDS), obtained from Sigma. In other exemplary implementations, the detergent used is Zwittergent 3-14, obtained from Calbiochem.

Amyloids are fibrous cross-β protein aggregates. Numerous proteins are capable of converting to amyloid-like fibrils with characteristics that include fibrillar morphology, protofilament substructure, cross-β diffraction pattern, an increase in β-structure, Congo red binding, and ThT binding. In exemplary implementations, the globular protein is converted to form amyloid-like fibrils, which allows for the converted protein to be identified by its amyloid-like properties.

The protein for treating the cancer may be selected based on the severity of the disease and the desired cytotoxicity to the cancer cells. In exemplary implementations, for greater cytotoxicity to the cancer cells is selected. The fibrillar proteins may include fibrillar proteins derived from the same protein types or more than one, more than two, more than three or more types. For example, the methods of treatment described above can administer rVP1 fibrillar proteins and fibrillar BSA together in one dosage or separately.

According to implementations, chromatography may be used in the process to convert the globular protein structure into a fibrillar protein structure and separate them. Generally, chromatography is accomplished using columns, though other methods such as those used for thin-layer chromatography may also be possible. Chromatography techniques include size exclusion, affinity, and ion-exchange. Though a batch-type production of fibrillar proteins is possible, utilizing a column process allows globular proteins to be converted into a fibrillar form in a rapid, steady, efficient, and continuous manner. Scaling-up this process is also possible with the usage of columns.

According to exemplary implementations, size exclusion chromatography with bead pore sizes of at least about 70 kDa is used. The bead pore size used may vary depending on various characteristics of the globular protein, for example its size. The pore size plays a role in allowing proteins to enter the bead matrix, thus leading to mechanical forces which contribute to protein unfolding/folding and enhance fibrillogenic ensemble. In exemplary implementations, the molecular sizing column used is a Superdex 200. In other exemplary implementations, the molecular sizing column used is a HW55S.

For column chromatography, a buffer solution containing low concentration(s) of detergent may be used to elute the column. In exemplary implementations, the molecular sizing column is eluted with a buffer solution containing 25 mM Tris-HCl (pH 8.0), 1 mM EDTA, 0.1 M NaCl, and 0.05% SDS. In other exemplary implementations, the molecular sizing column is eluted with a buffer solution containing 25 mM Tris-HCl, pH 8.0, 1 mM EDTA, 0.1 M NaCl, and 0.05% Zwittergent 3-14. The eluant may be collected as fractions and the fractions containing the fibrillar protein subsequently pooled together. The pooled fraction may then be further filtered to purify and isolate the fibrillar protein, for example dialyzing against PBS to remove SDS or Zwittergent 3-14.

According to implementations, human serum albumin (HSA) can be made into fibrillar human serum albumin by the processes disclosed herein for creating fibrillar proteins. According to implementations, human serum albumin has been confirmed convert to fibrillar form by the processes disclosed herein. With respect to creating fibrillar proteins, U.S. Pat. No. 7,488,800 is incorporated by reference.

The fibrillar HSA (F-HSA) was unexpectedly found to be at least as potent as recombinant capsid protein of foot and mouth disease virus (rVP1) in causing apoptosis in a variety of cancer cells. Among the advantages of using F-HSA instead of rVP1 as a cancer therapeutic is that HSA is a human endogenous protein. Thus, HSA or its derivatives with similar sequence and composition would be less likely than foreign proteins such as rVP1 to induce immunogenicity and neutralizing antibodies during clinical applications.

According to implementations, F-HSA was generated by dissolving HSA in a 1% SDS solution, passing through a Superdex-200 gel filtration column and eluting with a buffer solution containing 25 mM Tris-HCl (pH 8.0), 1 mM EDTA, 0.1 M NaCl, and 0.05% SDS (FIG. 1). After dialysis against PBS to remove the SDS, it was found that unlike HSA, the eluted F-HSA from the Superdex-200 column exhibited enhanced fluorescence level of amyloid-specific dye ThT in a dose-dependent manner.

Figure 18:
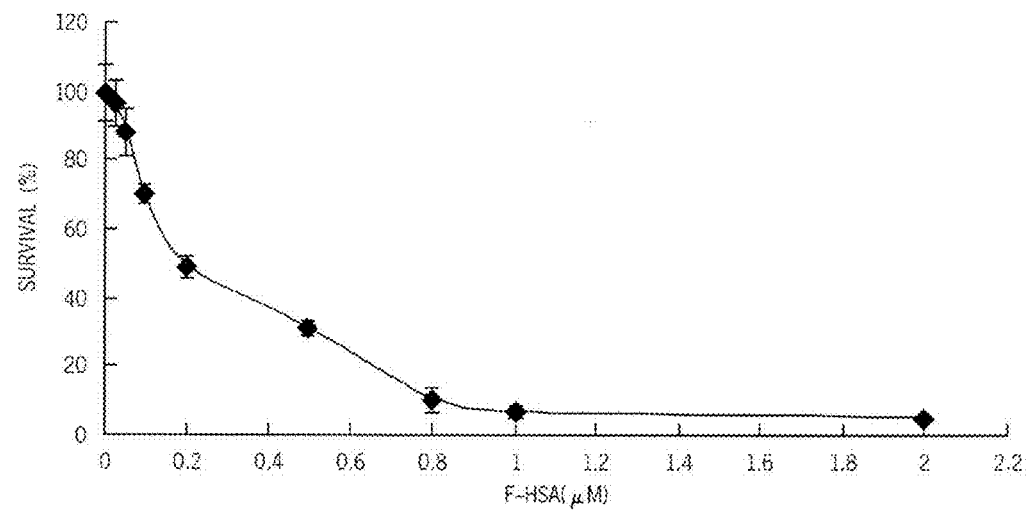
FIG. 18 is an implementation of experimental data showing the cytotoxic effects of F-HSA on prostate cancer cells.
Figure 19:
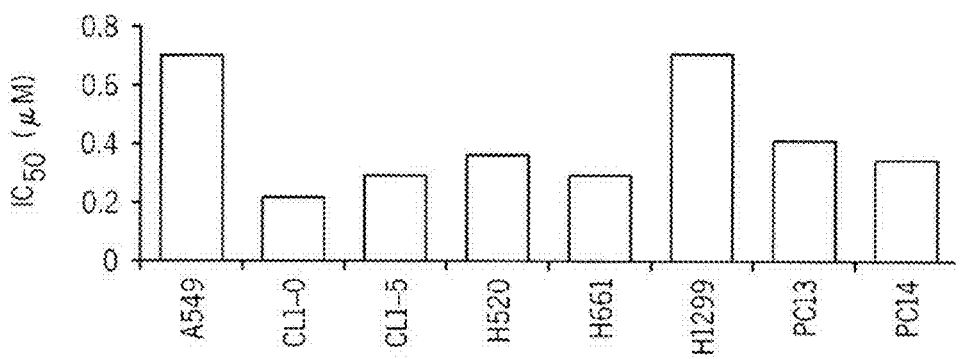
FIG. 19 is an implementation of experimental data showing the cytotoxic effects of F-HSA on lung cancer cells.

It was then determined that F-HSA induced cytotoxicity in cancer cells. As fibrillar serum albumin bound to receptors such as integrins on the cell surface while globular serum albumin could not, it is believed that the change of structure of serum albumin from globular to fibrillar form has enabled the proteins to selectively target cancer cells that expressed more integrin $\alpha 5\beta 1$ than normal cells. F-HSA inhibited breast cancer cell growth dose dependently including TS/A (murine mammary adenocarcinoma) and MDA-MB-231 (human mammary adenocarcinoma) cells with $IC_{50}$ of 0.15 (FIG. 13) and 0.48 μM (FIG. 14), respectively. F-HSA inhibited ovarian cancer cell SKOV3 growth with $IC_{50}$ of 0.6 μM (FIG. 15) and cervical cancer cell CaSki growth with $IC_{50}$ of 1.1 μM (FIG. 16). F-HSA also induced cytotoxicity in prostate cancer cells PC-3 and 22Rv1 with $IC_{50}$ of 0.35 (FIG. 17) and 0.2 μM (FIG. 18), respectively. In addition, F-HSA induces cytotoxicity in a number lung cancer cell lines (FIG. 19).

According to implementations, therefore, a method for treating cancer is disclosed. The method comprises the steps of providing HSA, changing the HSA into a fibrillar structure, and administering a therapeutically effective amount of the F-HSA to a patient in need thereof. Conversion of the HSA into fibrillar form increases its cytotoxic effects on target cells.

In exemplary implementations, the cancer is a kidney, breast, lung, prostate, liver, cervical, or ovarian cancer. In exemplary implementations, the fibrillar HSA plays a role in inducing cancer cell apoptosis by modulating the Akt signaling pathway. In some instances, the fibrillar HSA modulates integrin $\alpha 5\beta 1$ or $\alpha v\beta 3$ which leads to the deactivation of Akt. In other instances, fibrillar HSA binds to integrin and causes cellular apoptosis mainly through the integrin/FAK/Akt/GSK-3β/caspase-3 pathway.

The fibrillar HSA protein, derivate, ortholog, or other protein having substantial identity to HSA for treating the cancer may be selected based on the severity of the disease and the desired cytotoxicity to the cancer cells. In exemplary implementations, for greater cytotoxicity to the cancer cells, a protein with an RGD motif or greater molecular weight is selected. RGD motif is a ligand for integrins. It has been shown that fibrillar proteins induced cell death via modulating integrin/Akt signaling pathway. It has been found that fibrillar proteins with RGD motifs, like rVP1-S200 and FN-S200, were more cytotoxic than those without RGD motifs such as BSA-S200 and rVP3-S200.

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions, and truncations in the polypeptide encoded by the reference sequence, as discussed herein.

A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, and deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

An "ortholog" denotes a polypeptide or polynucleotide obtained from another species that is the functional counterpart of a polypeptide or polynucleotide from a different species. Sequence differences among orthologs are the result of speciation.

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of compositions having cytotoxic activities are contemplated as being encompassed by the present invention, providing that the variations in the amino acid of HSA sequence maintain at least 75%, at least 80%, at least 90%, at least 95%, or at least 99% identity. In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Fragments or analogs of proteins or peptides of the present invention can be readily prepared by those of ordinary skill in the art. Preferred amino- and carboxy-termini of fragments or analogs occur near boundaries of functional domains. Structural and functional domains can be identified by comparison of the nucleotide or amino acid sequence data to public or proprietary sequence databases. Preferably, computerized comparison methods are used to identify sequence motifs or predicted protein conformation domains that occur in other proteins of known structure or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Effective amino acid substitutions are those which: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various mutations of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991), which are each incorporated herein by reference.

The term "polypeptide fragment" as used herein refers to a polypeptide that has an amino-terminal or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long.

Generally, the method of making fibrillar proteins involves dissolving proteins in a SDS or other suitable detergents solution; applying the dissolved proteins through a gel filtration column with a pore size that can separate proteins of 70 kDa molecular weight and above; eluting the protein from the column; and dialyzing the eluate against buffered saline to remove the SDS or detergents.

In the first step, the globular protein is generally dissolved into solution form. In an example, the globular protein is dissolved in PBS with surfactants. Surfactants, also referred to herein as detergents, are substances that lower the surface tension of water and increase the solubility of organic compounds. Detergents may be ionic, which includes cationic, anionic, and zwitterionic detergents, as well as non-ionic. Detergents play a role in disrupting non-covalent bonds in proteins, thereby denaturing the proteins such that they lose their native shape or conformation. In exemplary implementations, the detergent used is sodium dodecyl sulfate (SDS), obtained from Sigma. In other exemplary implementations, the detergent used is Zwittergent 3-14, obtained from Calbiochem.

In some aspects of the method, size exclusion chromatography with bead pore sizes of at least about 70 kDa is used. The bead pore size used may vary depending on various characteristics of the globular protein, for example its size. The pore size plays a role in allowing proteins to enter the bead matrix, thus leading to mechanical forces which contribute to protein unfolding/folding and enhance fibrillogenic ensemble. In exemplary implementations, the molecular sizing column used is a Superdex 200. In other exemplary implementations, the molecular sizing column used is a HW55S. Other details of the method to produce fibrillar proteins may be found in US Pat Pub No. 2008/0800186, disclosure of which is incorporated herein by reference.

The following examples are put forth so as to provide those of ordinary skill in the art with a complete disclosure and description of how to make and use the subject invention, and are not intended to limit the scope of what is regarded as the invention.

EXPERIMENTAL

Example 1

Methods

Cell Lines and Culture.

SK-OV-3 cells (human ovarian carcinoma cell line; ATCC HTB-77) and SK-OV-3ip.1 cells, and CaSki cells (human cervical carcinoma cell line; ATCC CRL-1550) were maintained at 37° C. in McCoy's 5A and RPMI-1640 medium, respectively. MDA-MB-231 cells (human mammary adenocarcinoma cell line; ATCC HTB-26) and TS/A cells (murine mammary adenocarcinoma cell line) were maintained at 37° C. in Dulbecco's modified Eagle's medium (DMEM)/F12 medium and DMEM, respectively. PC-3 cells (human prostate adenocarcinoma cell line; ATCC CRL-1435) and 22Rv1 cells (human prostate carcinoma cell line; ATCC CRL-2505) were maintained at 37° C. in RPMI-1640 medium. All medium were supplemented with 10% fetal bovine serum (FBS), 2 mM L-glutamine, 100 units/ml penicillin, and 100 µg/ml streptomycin.

Cytotoxicity Assay.

Cell survival was determined by MTT assay or WST-1 assay. In brief, $1\times10^5$ cells/well of tumor cells were seeded in 96-well plates in serum-free medium and incubated for 1 h. Treatment of cells with a series of concentrations of rVP1, F-BSA, or F-HSA was carried out in serum-free medium for 24 h at 37° C. After treatment, MTT solution was added to each well (0.5 mg/ml), followed by 4 h incubation. The viable cell number is directly proportional to the production of formazan, which, following solubilization with isopropanol, can be measured spectrophotometrically at 570 nm by an ELISA plate reader. Data expressed as a percentage of untreatment condition and presented as the mean±S.D.

WST-1 assay was carried out according to the manufacturer's instructions (Roche, Mannheim, Germany). In brief, $2\times10^4$ cells were added to 100 µl media per well on a 96 well plate and incubated at 37° C. in 5% $CO_2$ overnight in a humidified incubator. The cells attached to the wells were incubated in serum-free medium and treated with serial dilutions of rVP1. After incubation at 37° C. in 5% $CO_2$ for 16 h to allow the drug to take effect, 10 µl WST-1 reagent was added to each well, and the plate was then mixed on a shaking table at 150 rpm for 1 min. After incubation at 37° C. in 5% $CO_2$ for another 2 h to allow the WST-1 reagent to be metabolized, the proportion of surviving cells were determined by optical density (450 nm test wavelength, 690 nm reference wavelength). The percentage of surviving cells was calculated as $(O.D._{treatment}/O.D._{control})\times100\%$ while the percentage of growth inhibition was calculated as $[1-(O.D._{treatment}/O.D._{control})]\times100\%$. $IC_{50}$ is the concentration at which the reagent yields 50% inhibition of the cellular viability.

Cell Migration and Invasion Assay.

Cell migration and invasion assays were performed following Boyden chamber migration and invasion assay (Corning). The 8-µm pore membranes of the upper chambers were coated with 20 µg/ml fibronectin for cell migration assay or 40 µg/ml Matrigel for cell invasion assay and placed in a well with 1 ml of PBS and incubated for 2 hours at 37° C. Cancer cells ($1\times10^5$) were re-suspended in serum-free medium and plated onto the upper chamber for 1 h. A various concentration of fibrillar proteins such as rVP1 were added into the upper chamber then the culture medium (10% FBS medium) was added to the lower chamber. Cells were incubated for 24 hours at 37° C. At the end point of incubation, cells on the upper side of the membrane were removed by wiping it with a cotton swab, and cells that had migrated onto the lower membrane surface were dissociated by using cell dissociation solution (Sigma) and counted by flow cytometer (BD company).

Establishment of Metastatic Implantation in a Murine Model of TS/A Mammary Adenocarcinoma in BALB/c Mice.

Murine TS/A mammary adenocarcinoma cells were cultured in DMEM supplemented with 10% FBS, 2 mM L-glutamine, 100 U/ml penicillin and 100 µg/ml streptomycin in a humidified atmosphere of 95% air and 5% $CO_2$ at 37° C. After harvest, TS/A cells ($3\times10^5$/100 µl PBS/mouse) were intravenously injected into the lateral tail vein of nine mice per group. Control medium or fibrillar proteins such as F-HSA were given by i.v. route once every two days for ten times. Finally, three mice per group were sacrificed and others were used for survival assay In another experiment, murine TS/A mammary adenocarcinoma cells were first cultured in DMEM supplemented with 0% FBS, 2 mM L-glutamine, 100 U/ml penicillin and 100 µg/ml streptomycin with or without fibrillar proteins such as rVP1 (0.1-0.2 µM) treatment in a humidified atmosphere of 95% air and 5% $CO_2$ at 37° C. After harvest, the TS/A cells pretreated with or without rVP1 were intravenously injected ($3\times10^5$/100 µl PBS/mouse) in the lateral tail vein of nine mice per group, respectively. After 14 days, all mice were sacrifice and harvested the lungs.

Establishment of Metastatic Xenograft Implantation in a Murine Model of Human Breast Cancer.

Human MDA-MB-231 mammary adenocarcinoma cells were cultured in DMEM/F12 supplemented with 10% FBS, 2 mM L-glutamine, 100 U/ml penicillin and 100 µg/ml streptomycin in a humidified atmosphere of 95% air and 5% $CO_2$ at 37° C. After harvest, MDA-MB-231 cells ($3\times10^5$/100 µl PBS/mouse) were intravenously injected into the lateral tail vein of nine mice per group. One day after tumor injection, fibrillar proteins such as F-HSA (1 mg/Kg BW) were given by i.v. route once every two days for ten times while control group were injected with medium only. Three mice per group were sacrificed at this time point and the rest of mice were kept to measure the survival rate.

Establishment of Orthotropic Xenograft Implantation in a Murine Model of Human Prostate Cancer.

Human PC-3 prostate cancer cells were cultured in RPMI-1640 medium supplemented with 10% FBS, 2 mM L-glutamine, 100 U/ml penicillin and 100 µg/ml streptomycin in a humidified atmosphere of 95% air and 5% $CO_2$ at 37° C. After harvest, PC-3 cells were washed and orthotopically injected in prostate ($1\times10^5$/20 µL PBS/mouse). In one group, four wks after PC-3 implantation, fibrillar proteins such as rVP1 (25 mg/kg) was given by i.v. route, while in the other group rVP1 was given 10 wks after cancer implantation. The same amount of rVP1 was administered three times per week for 6 weeks and at the end of rVP1 treatment, 3 mice were sacrificed in each group to detect the cancer metastasis. The rest of mice were kept to measure the survival rate.

Establishment of Metastatic Xenograft Implantation in a Murine Model of Human SK-OV-3 Ovarian Cancer.

Animal studies were performed in compliance with the guidelines for the care and use of laboratory animals of the National Defense Medical Center, Taiwan. BALB/cAnN- Foxn1 female nude mice, 8 weeks old, obtained from National Animal Center, Taiwan, were inoculated with $5\times10^6$ SK-OV-3 cancer cells per mouse by intraperitoneal injection 6 days after SK-OV-3 implantation, mice were treated with fibrillar proteins (eg. rVP1, 15 mg/Kg BW) or PBS (control) and the treatments repeated every other day for 60 days. The survival percentage and body weights were recorded until the mice died or 340 days after tumor implantation.

Isolation of SK-OV-3Ip.1 Cells.

Mice were sacrificed by instant cervical dislocation 60 days after SK-OV-3 cell implantation. Three ml of PBS was then injected to the belly and the intraperitoneal cells were retrieved (about 2 ml) using a 5-ml syringe and a 25 gauge×1" needle. The cells were centrifuged at 200×g for 5 min at 4° C. and the cell pellet collected. To remove red blood cells, 5 times cell pellet volume of $NH_4Cl$ (0.144 M) and ½ times cell pellet volume of $NH_4HCO_3$ (0.01 M) were added and incubated at 4° C. for 5 min. The cells were centrifuged at 200×g for 5 min at 4° C. and the cell pellet was collected. Cells were cultured in McCoy's 5A medium with 20% FBS in a 5% $CO_2$-humidified atmosphere at 37° C. for 3 days before Western blot analysis of HER-2 receptor levels, using standard Western blot techniques following resolution by SDS-PAGE on a 8-16% gradient gel (Invitrogen).

Histopathology.

The organs were fixed in 10% neutral buffered formalin. The tissues were farther embedded in paraffin, cut at 4 μm sections, stained with hematoxylin and eosin (H&E) for light microscopy.

Statistical Analysis.

Figure 2:
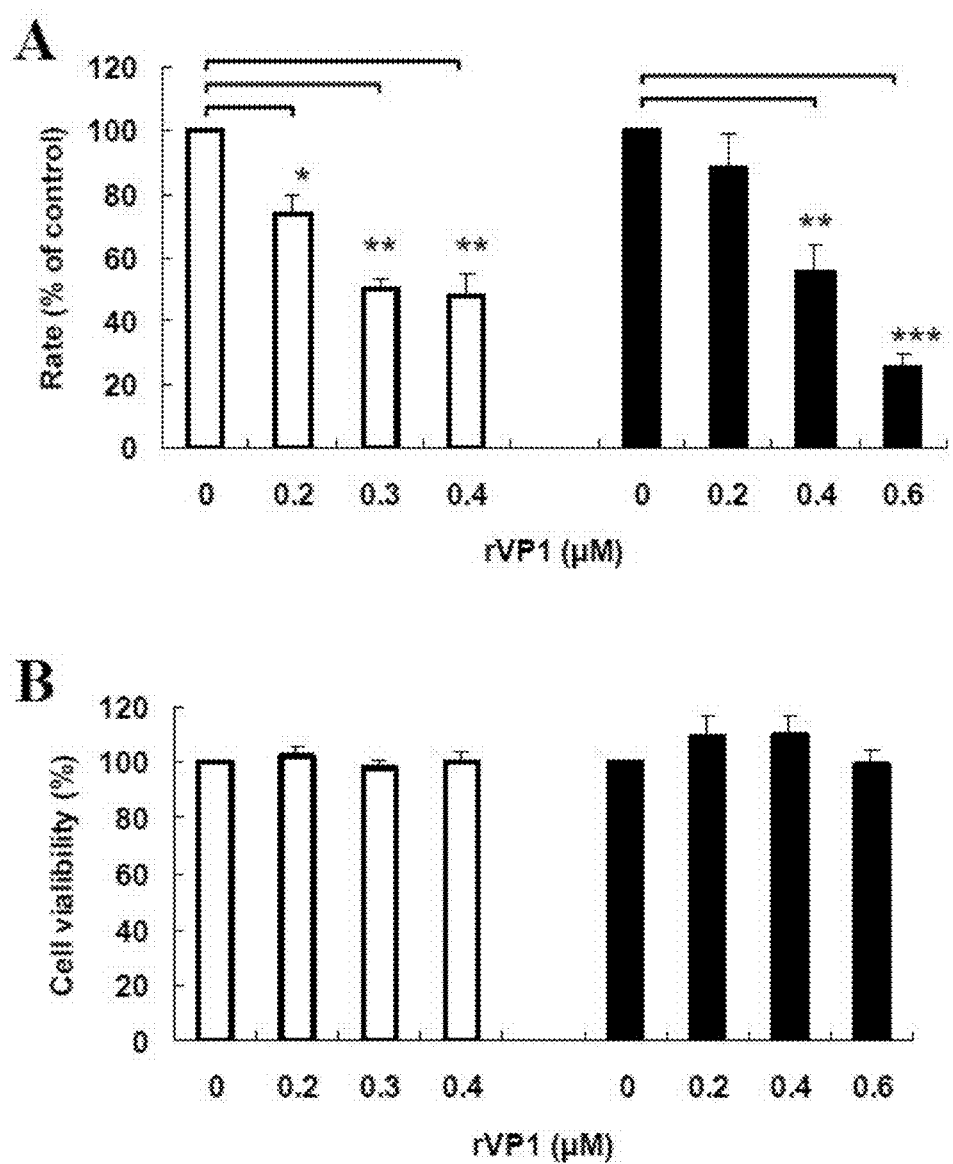
FIG. 2. The effects of rVP1 on cell invasion and cytotoxicity in SK-OV-3 cells and CaSki cells. (A) Cell invasion of SK-OV-3 cells and CaSki cells with rVP1 treatment for 24 hrs was measured by using Boyden chamber assay. rVP1 significantly suppressed tumor cell invasion (B) Cell cytotoxicity of SK-OV-3 cells and CaSki cells with rVP1 treatment for 24 hrs was measured by using MTT assay. 0.2 µM to 0.4 µM rVP1 in SKOV-3 cells and 0.2 µM to 0.6 µM rVP1 in CaSki cells did not affect cell viability. White bar, SKOV-3 cells; black bar, CaSki cells. Data represent means±S.D. (n=3). *: $P<0.05$; : $P<0.01$; *: $P<0.001$.
Figure 3:
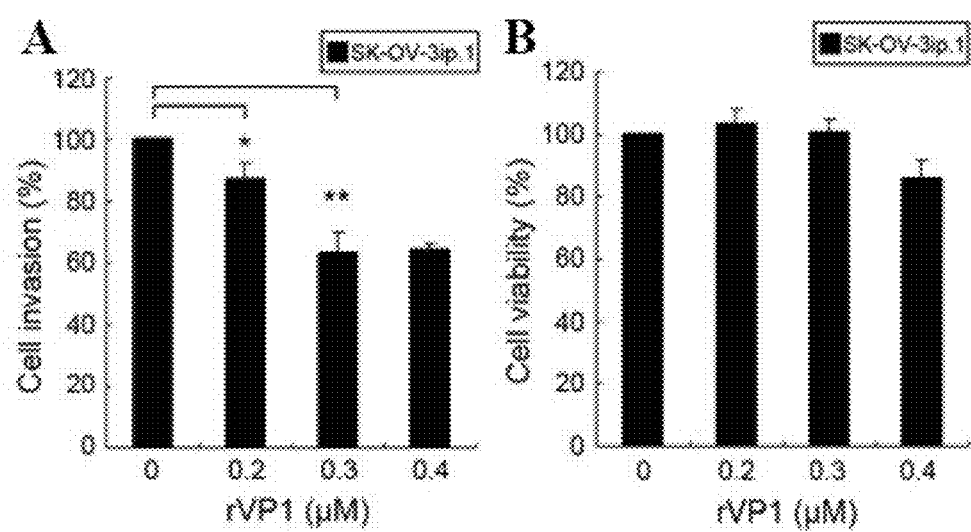
FIG. 3. The effects of rVP1 on cell invasion and cytotoxicity in SK-OV-3ip.1 cells. (A) SK-OV-3ip.1 cells were plated onto the upper chamber for 1 hour followed by rVP1 treatment for 24 h. After incubation, cells from the lower membrane surface were dissociated and counted. (B) SK-OV-3ip.1 cells were treated with rVP1 for 24 h then WST-1 assays were performed. Cell survival rates were determined by measuring the absorbance at 450 nm (690 nm as reference). The percentage of cell survival was calculated as $(O.D._{treatment}/O.D._{control}) \times 100\%$. Data represent means±S.D. (n=3). *, $P<0.05$ and **, $P<0.01$ were relative to control.

All data were expressed as means±standard error and estimated with Microsoft Excel. For the survival data, the log-rank test was used to determine differences between groups treated with or without drugs. The Student's t-test and ANOVA were performed to assess overall differences between the different treatments. Values of $P<0.05$, $P<0.01$, and $P<0.001$ were considered statistically significant.

rVP1 suppressed cell invasion and/or migration in MDA-MB-231 cells, PC-3 cells, 22Rv1 cells, SK-OV-3 cells, CaSki cells, and SK-OV-3ip.1 cells in vitro To investigate whether rVP1 suppressed tumor cell invasion and/or migration, cell invasion and/or migration were measured using Boyden chamber assay. After various concentrations (0.1 μM to 0.2 μM rVP1 in human mammary adenocarcinoma cell line MDA-MB-231 cells, human prostate adenocarcinoma cell line PC-3 cells, human prostate carcinoma cell line 22Rv1 cells; 0.2 μM to 0.4 μM rVP1 in human ovarian carcinoma cell line SK-OV-3 cells and SK-OV-3ip.1 cells; 0.2 μM to 0.6 μM rVP1 in human cervical carcinoma cell line CaSki cells) of rVP1 treatment, cell invasion and/or migration were significantly suppressed. Of note, these concentrations of rVP1 did not affect cell viability as determined by using MTT assay or WST-1 assay (FIGS. 1-3). Therefore, rVP1 can significantly suppress metastasis of human breast cancer, prostate cancer, cervical cancer, and ovarian cancer cell lines in vitro.

Example 2 rVP1 Suppressed Tumor Cell Metastasis In Vivo

A. In Vitro rVP1-Treated MDA-MB-231 Cells Followed by i.v. Injection into BALB/c Mice.

Figure 4:
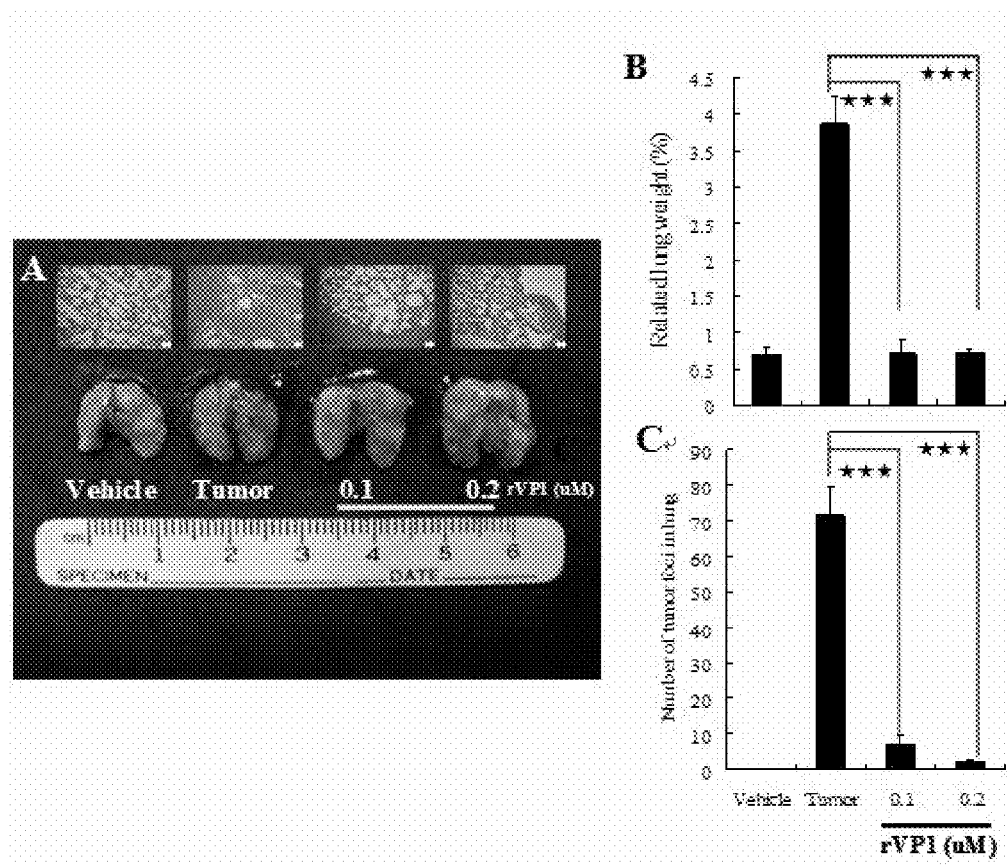
FIG. 4. The metastatic ability of MDA-MB-231 cells was lost after rVP1 treatment in vivo. 0.1 µM and 0.2 µM rVP1-treated MDA-MB-231 cells in vitro for 24 hrs then harvested and intravenously injected in mice through tail vein. After 14 days, sacrifice was performed. The gross appearance (A) and histopathology examination (B and C) of lung in three different groups of mice were measured. rVP1 significantly inhibited metastatic ability of MDA-MB-231 cells. ***: $P<0.001$.

We then examined whether pretreated MDA-MB-231 human mammary adenocarcinoma cells with rVP1 for 24 h to inhibit metastatic ability in vitro then injected the cells intravenously in mice could reduce their metastasis in mice lung as compare with MDA-MB-231 cells without rVP1 pretreatment. Data showed that 0.1 and 0.2 μM rVP1-treated MDA-MB-231 cells significantly decreased cancer cells metastasis in mice lung tissue (FIG. 4A). The related lung weight and the number of tumor foci in lung were also significantly decrease compared to tumor group without rVP1 treatment (FIGS. 4B-C).

B. Orthotropic PC-3 Xenograft Model.

Figure 5:
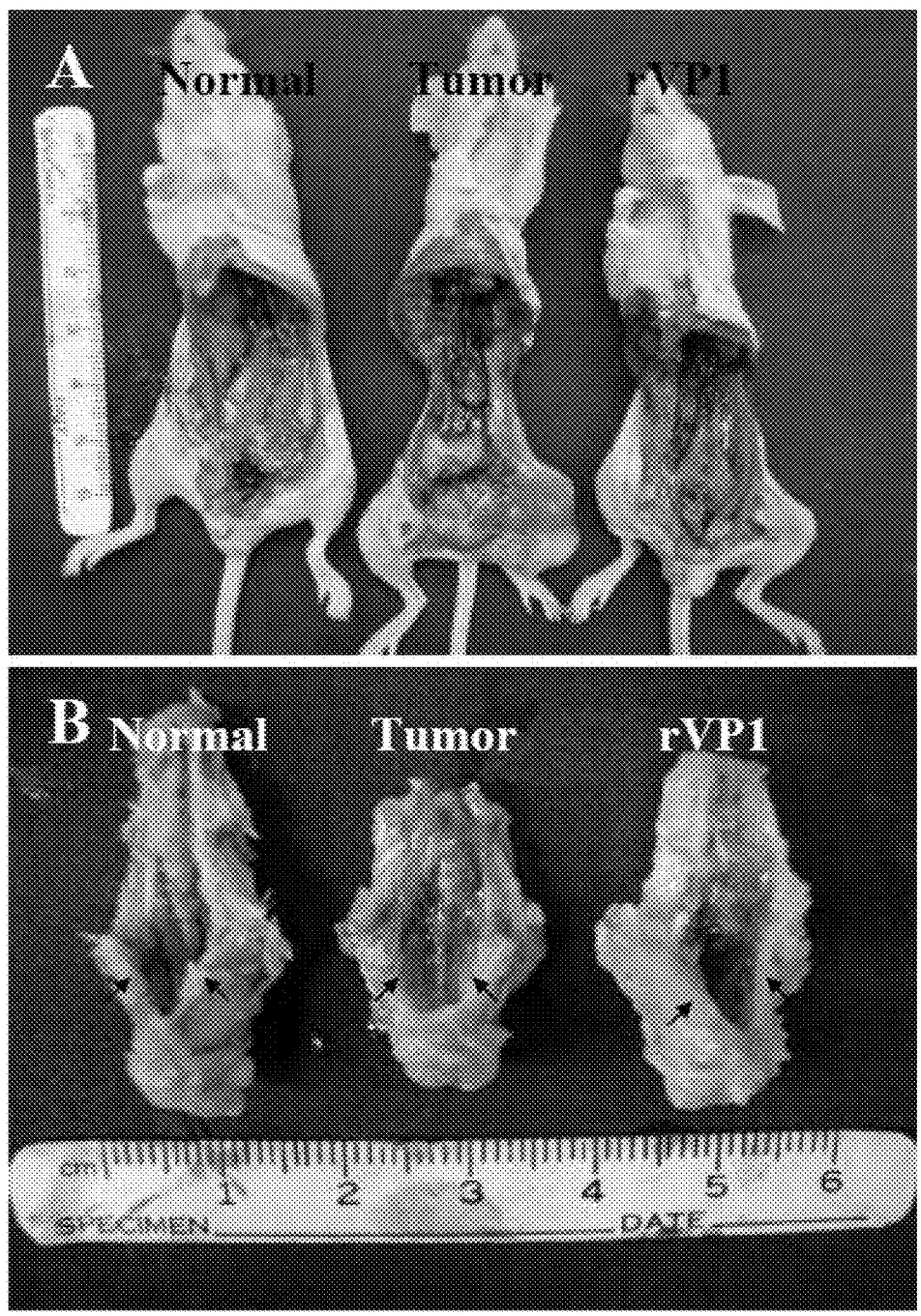
FIG. 5. rVP1 suppressed PC-3 cells metastasized to lymph nodes and inhibited osteolysis in pelvic bones. (A) The lymph nodes of normal and tumor bearing mice with or without rVP1 treatment. (B) The pelvic bones of normal and tumor bearing mice with or without rVP1 treatment (arrow).

We also examined whether rVP1 could suppress prostate cancer metastasis in vivo. PC-3 human prostate adenocarcinoma cells were first orthotopically implanted to nude mice' prostate and 4-wks or 10-wks after implantation, rVP1 (25 mg/kg) was then injected intravenously three times every week for 6 wks. At the end of rVP1 treatment, we sacrificed mice to undertake autopsy. Our data showed that rVP1 significantly suppressed PC-3 cells metastasized to lymph nodes (Table 1, FIG. 5A) and pelvic bones, and inhibited osteolysis in pelvic bones (FIG. 5B).

TABLE 1

The percentage and location of metastatic lymph nodes with rVP1 treatment in PC-3-implanted nude mice.

|  | Tumor | rVP1 (given 4 wks after tumor implantation) | Tumor | rVP1 (given 10 wks after tumor implantation) |
| --- | --- | --- | --- | --- |
| Renal nodes | 66.67% (2/3) | 0% (0/3) | 100% (3/3) | 0% (0/3) |
| Lumbar nodes | 100% (3/3) | 0% (0/3) | 100% (3/3) | 0% (0/3) |
| Sacral node | 0% (0/3) | 0% (0/3) | 66.67% (2/3) | 0% (0/3) |
| Sciatic node | 0% (0/3) | 0% (0/3) | 66.67% (2/3) | 0% (0/3) |
| Inguinal node | 33.33% (1/3) | 0% (0/3) | 33.33% (1/3) | 0% (0/3) |

C. Metastatic SK-OV-3 Xenograft Model.

Figure 6:
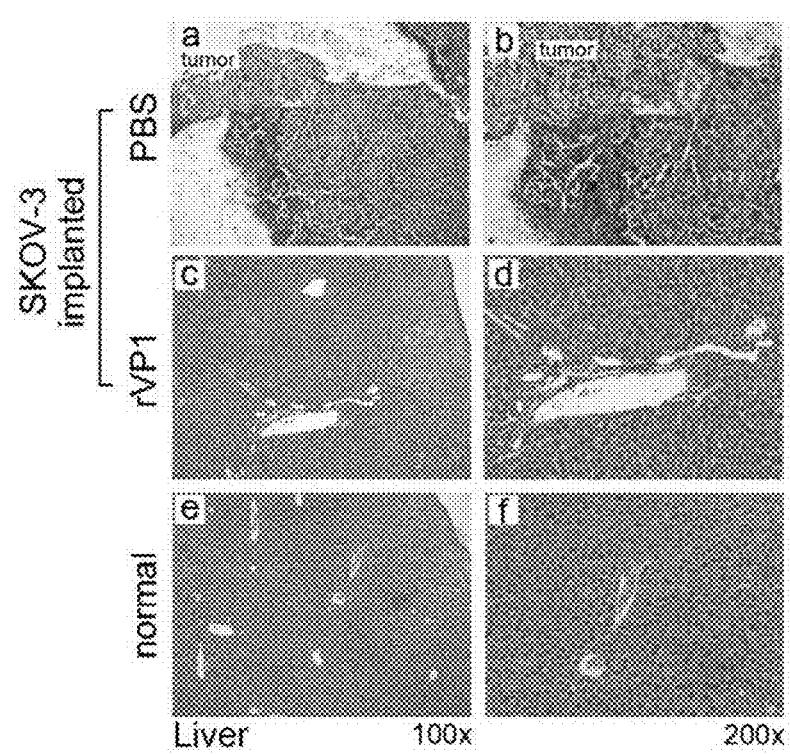
FIG. 6. In vivo histological appearance of liver tumor metastasis from SK-OV-3 implanted nude mice were prevented by rVP1. Representative liver sections with H&E stain from rVP1 treated and nontreated mice. BALB/cAnN-Foxn1 female nude mice were implanted with $5 \times 10^6$ SK-OV-3 cancer cells per mouse by intraperitoneal injection. (a-b) After 60 days, liver from PBS-treated SK-OV-3 bearing mice were surrounded by tumor cells. (c-d) 340 days after SK-OV-3 implantation, liver from rVP1-treated mice did not show apparent invasion. (e-f) Liver from normal mouse (i.e., without SK-OV-3 implantation).

Our in vitro data showed that rVP1 suppressed SK-OV-3 human ovarian carcinoma cell invasion. To examine whether rVP1 could also suppress SK-OV-3 ovarian cancer metastasis in vivo, metastatic xenograft implantation in a murine model of human SK-OV-3 ovarian cancer was established. We found that after 60 days, livers from PBS-treated SK-OV-3 bearing mice were surrounded by tumor cells. In the SK-OV-3 bearing mice injected with rVP1 (15 mg/kg) intraperitoneally every other day for 60 days, on the other hand, we did not observe any apparent tumor invasion of their livers (FIG. 6).

Example 3

Figure 7:
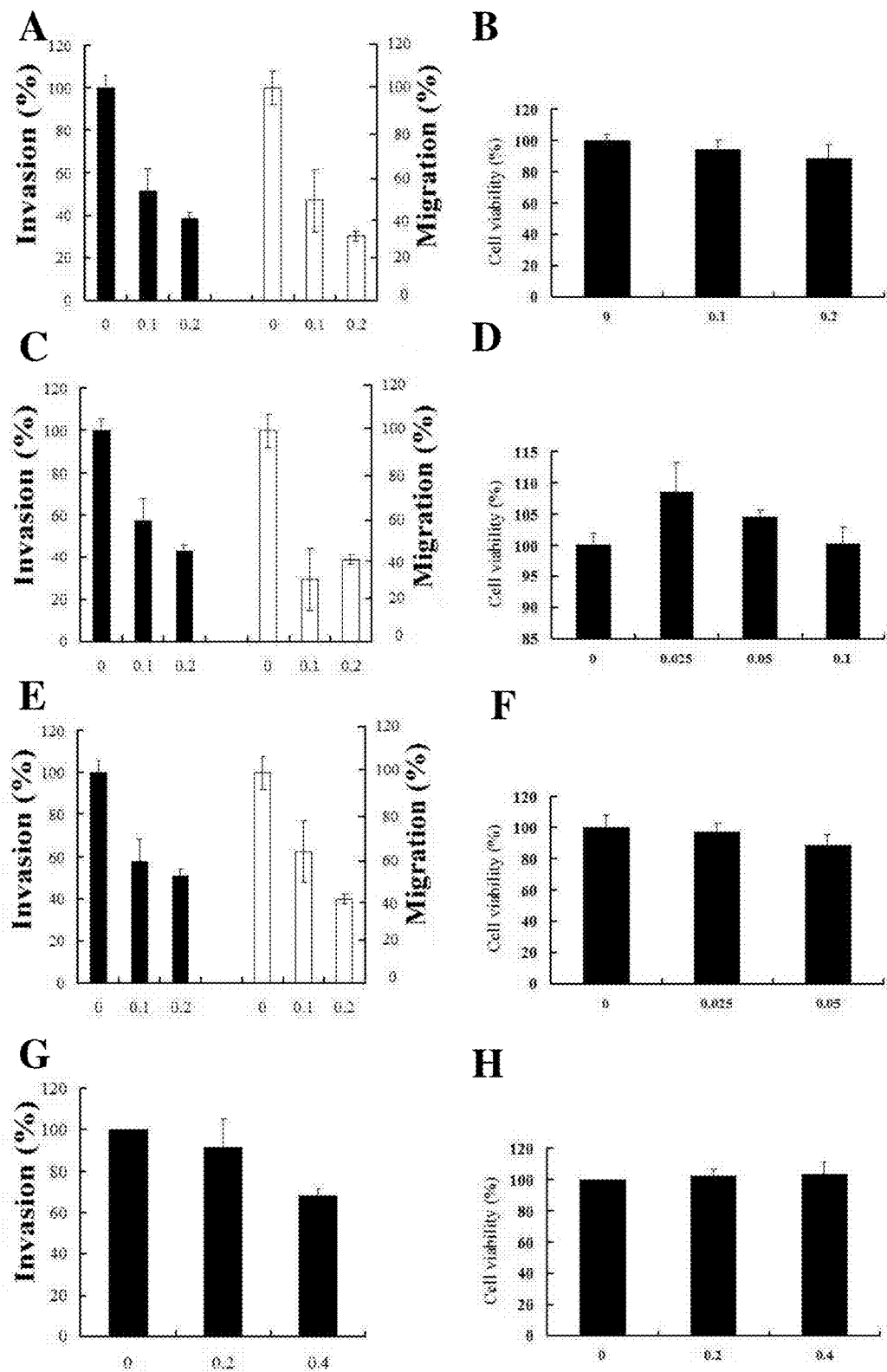
FIG. 7. The effects of F-HSA on cell migration, invasion and cytotoxicity in MDA-MB-231 cells, PC-3 cells, 22Rv1 cells, and CaSki cells. In vitro migration and invasion assay, F-HSA significantly inhibited cell invasion (black bar) and migration (white bar) in MDA-MB-231 cells (A), PC-3 cells (C), 22Rv1 cells (E), and CaSki cells (G) by using Boyden chamber assay. The effects of F-HSA on cytotoxicity in MDA-MB-231 cells, PC-3 cells, 22Rv1 cells, and CaSki cells by using MTT assay. (B, D, F, and H). Migration and invasion were represented as percentage of the number of treated cells to that of untreated cells. Shown were the means±S.D. of three independent experiments with three replicates in each. : $P<0.01$ and *: $P<0.001$ were relative to untreated cells.
Figure 8:
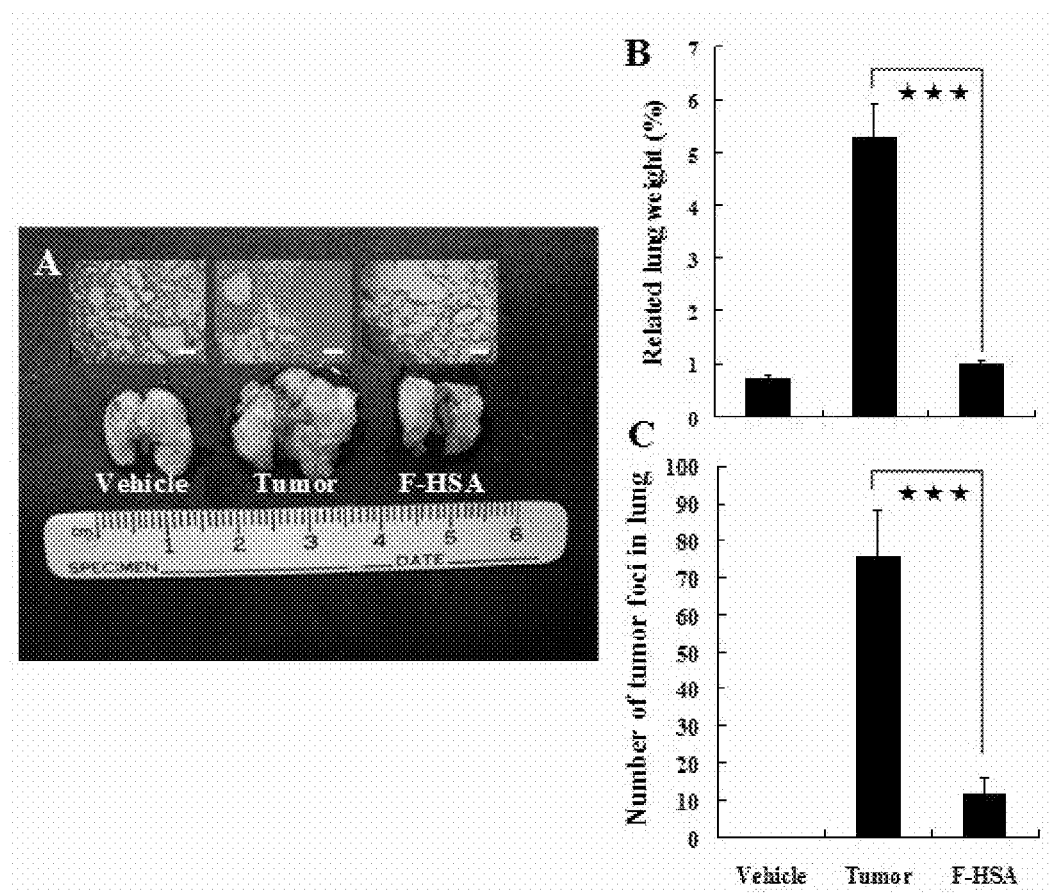
FIG. 8. F-HSA suppressed TS/A tumor cell metastasis in vivo. (A) The gross appearance and histopathology examination of lung from mice with or without F-HSA treatment. (B & C) The related lung weight and the number of tumor foci in lung from mice with or without F-HSA treatment. ***: $P<0.001$.
Figure 9:
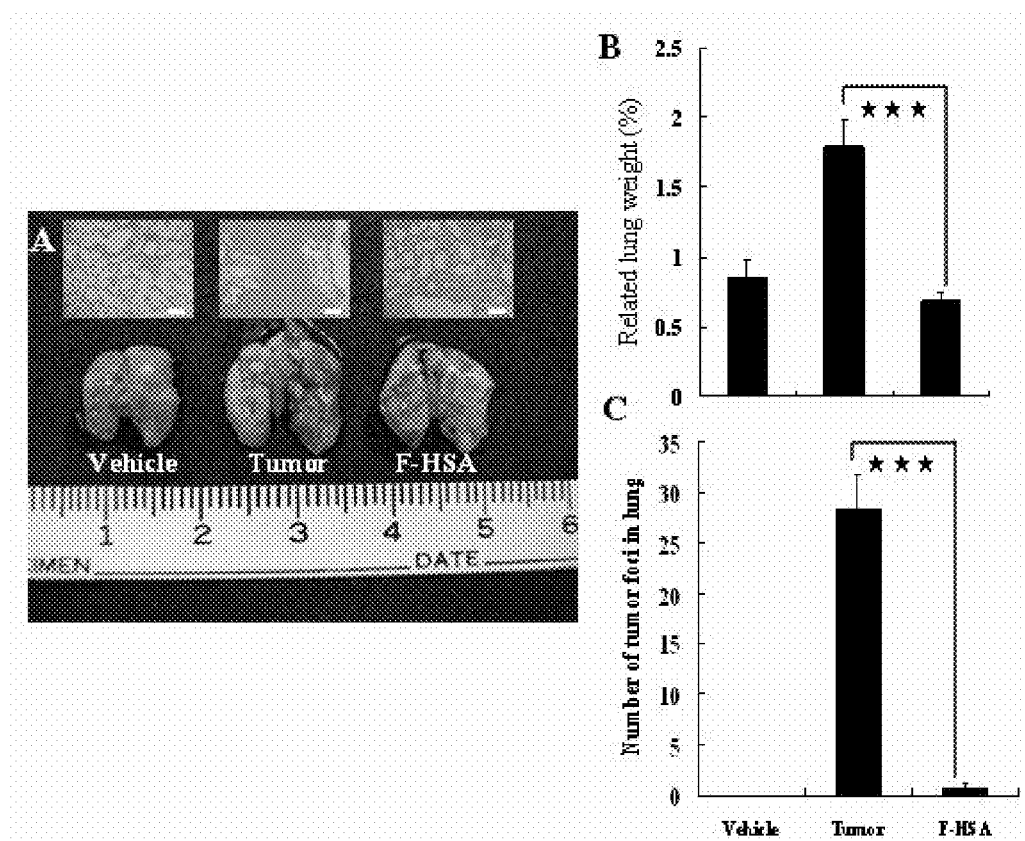
FIG. 9. F-HSA suppressed MDA-MB-231 tumor cell metastasis in vivo. (A) The gross appearance and histopathology examination of lung from mice with or without F-HSA treatment. (B & C) The related lung weight and the number of tumor foci in lung with or without F-HSA treatment. ***: $P<0.001$.

F-HSA Suppressed Tumor Cell Invasion and/or Migration in MDA-MB-231 Cells, PC-3 Cells, 22Rv1 Cells and CaSki Cells In Vitro To examine whether other fibrillar proteins such as F-HSA also suppressed cancer cell invasion and/or migration, the effect of F-HSA on cancer cell invasion and/or migration were measured by using Boyden chamber assay. After being treated with various concentrations of F-HSA (0.1 μM to 0.2 μM F-HSA in MDA-MB-231 cells; 0.025 to 0.1 μM F-HSA in PC-3 cells; 0.025 to 0.05 μM F-HSA in 22Rv1 cells; 0.2 to 0.4 μM F-HSA in CaSki cells), the invasion and/or migration abilities of a variety of cancer cells were significantly suppressed. It is of note that at these concentrations, F-HSA did not affect cell viability by using MTT assay (FIG. 7).

Example 4

F-HSA Suppressed Tumor Cell Metastasis In Vivo

To further examine whether F-HSA could suppress tumor cell metastasis in vivo, murine mammary adenocarcinoma TS/A cells were intravenously injected into the lateral tail vein of BALB/c mice or human mammary adenocarcinoma MDA-MB-231 cells were injected into nude mice respectively. F-HSA (1 mg/kg) was then injected intravenously at next day and then one time every two days for ten times. At the end of F-HSA treatment, mice were sacrificed to detect the metastasis of lungs. Our results showed that F-HSA significantly suppressed the metastasis of TS/A cells and MDA-MB-231 cells to lung (FIGS. 8A and 9A) as compared to TS/A or MDA-MB-231 bearing mice treated with control medium only. The relative lung weight and the number of tumor foci in lung of F-HSA treated TS/A or MDA-MB-231 bearing mice were significantly less than those of TS/A or MDA-MB-231 bearing mice without any drug treatment (FIGS. 8B-C and 9B-C).

Example 5

F-BSA Suppressed CaSki Cell Invasion In Vitro

Figure 10:
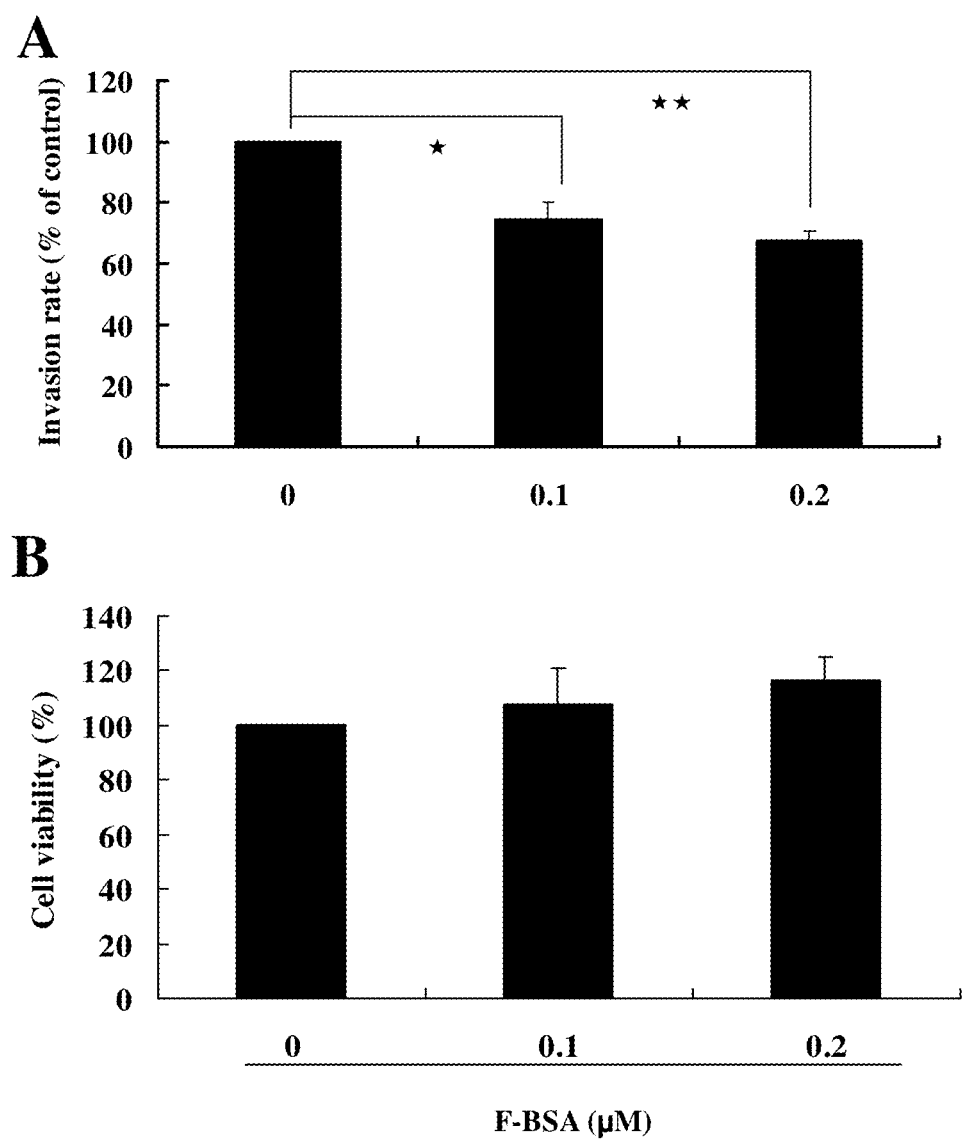
FIG. 10. The effects of F-BSA on cell invasion and cytotoxicity in CaSki cells. (A) Cell invasion of CaSki cells treated with F-BSA for 24 hrs was measured by Boyden chamber assay. F-HSA significantly suppressed tumor cell invasion. (B) The cytotoxicity of CaSki cells treated with F-BSA for 24 hrs was measured by MTT assay. F-HSA at 0.1 µM or 0.2 µM concentration had no effect on the cell viability of CaSki cells. Data represent means±S.D. (n=3). *: $P<0.05$; **: $P<0.01$.
Figure 11:
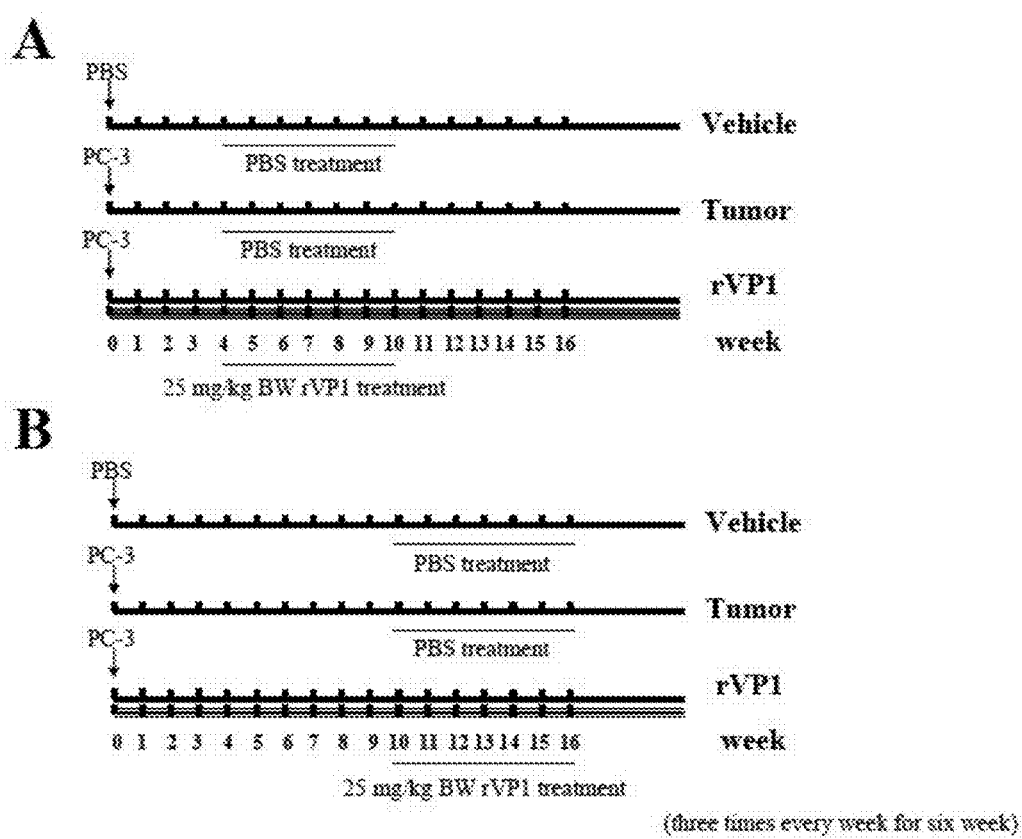
FIG. 11. A schedule of the tumor implantation with rVP1 treatment.

We also examined whether other fibrillar proteins such as F-BSA suppressed CaSki human cervical carcinoma cell invasion. Cell invasion was measured by using Boyden chamber assay. We found that at 0.1 μM-0.2 μM, although F-BSA did not affect cell viability as indicated by MTT assay, it significantly suppressed CaSki cell migration/invasion (FIG. 10).

Example 6

Figure 12:
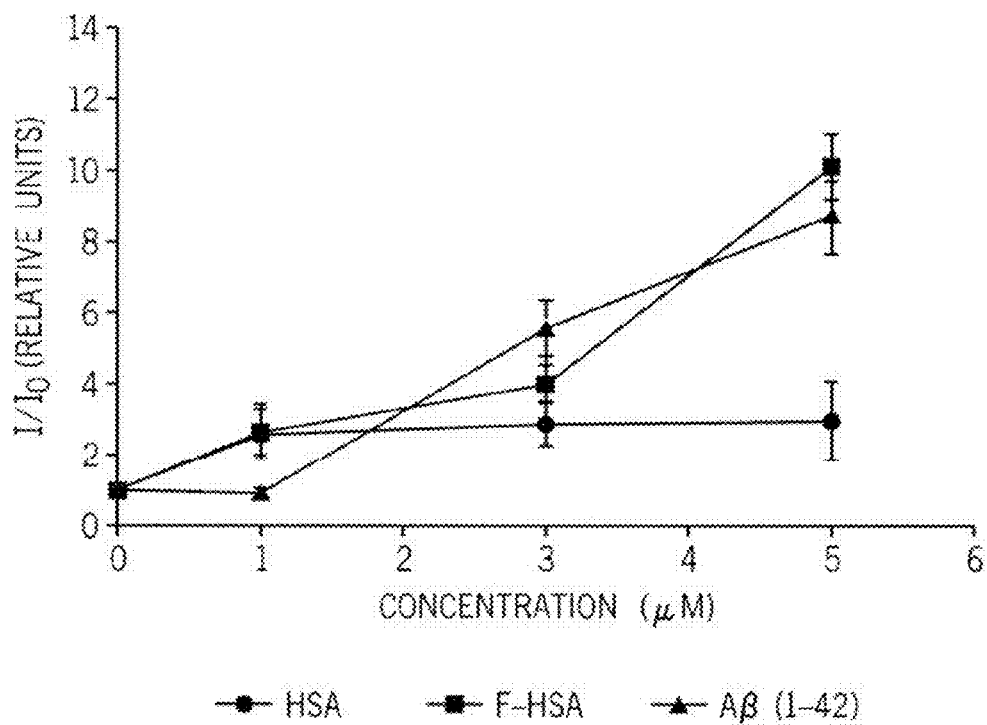
FIG. 12 is an implementation of experimental data showing a comparison of fluorescence level of increasing concentrations of F-HSA, HSA, and A β (1-42) after incubating with 20 µM amyloid-specific dye ThT for 1 h.

F-HSA Exhibits Enhanced Fluorescence Levels of Amyloid-Specific Dye ThT in a Dose-Dependent Manner FIG. 12 shows an implementation of experimental data shows that F-HSA, like amyloid fibrils Aβ (1-42), exhibit enhanced fluorescence level of amyloid-specific dye ThT in a dose-dependent manner as compared with BSA not processed by the Superdex-200 column. This result shows that F-HSA has a fibrillar structure like Aβ (1-42), whereas HSA has a globular structure. (Binding to ThT is one of the characteristics of amyloid-like proteins.)

Example 7

F-HSA has a Cytotoxic Effect on Breast Cancer Cells

Figure 13:
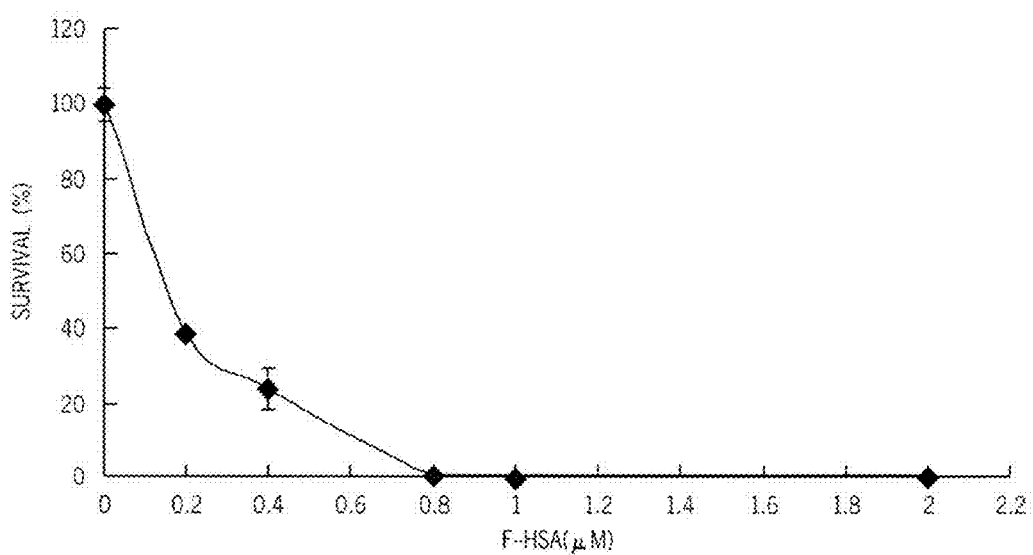
FIG. 13 is an implementation of experimental data showing the cytotoxic effects of F-HSA on breast cancer cells.
Figure 14:
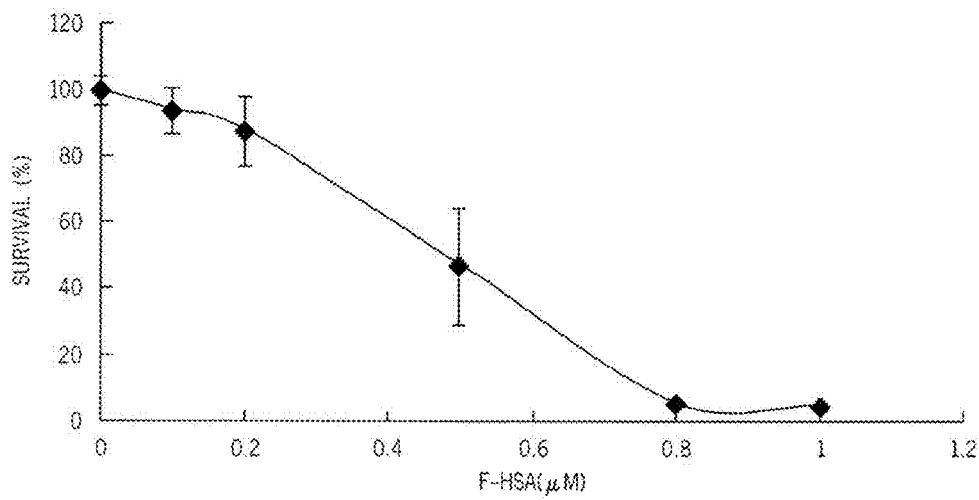
FIG. 14 is an implementation of experimental data showing the cytotoxic effects of F-HSA on breast cancer cells.

FIG. 13 shows F-HSA's cytotoxic effect in TS/A cells and FIG. 14 shows F-HSA's cytotoxic effect in MDA-MB-231 cells. Each respective cell type was treated for 16 h in serum-free culture medium with various concentrations of F-HSA. Cell viability was determined by the MTT assay. Globular HSA has no cytotoxic effect on normal or cancer cells.

Example 8

F-HSA has a Cytotoxic Effect on Ovarian and Cervical Cancer Cells

Figure 15:
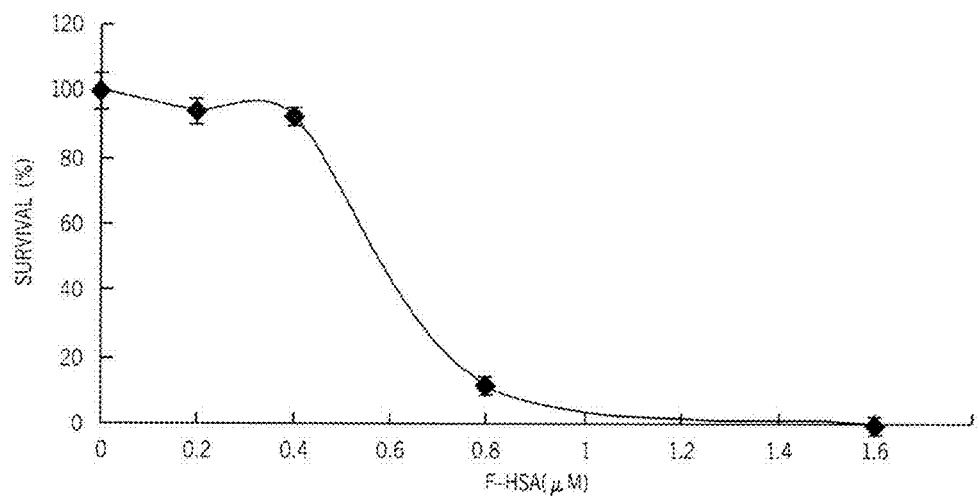
FIG. 15 is an implementation of experimental data showing the cytotoxic effects of F-HSA on ovarian cells.
Figure 16:
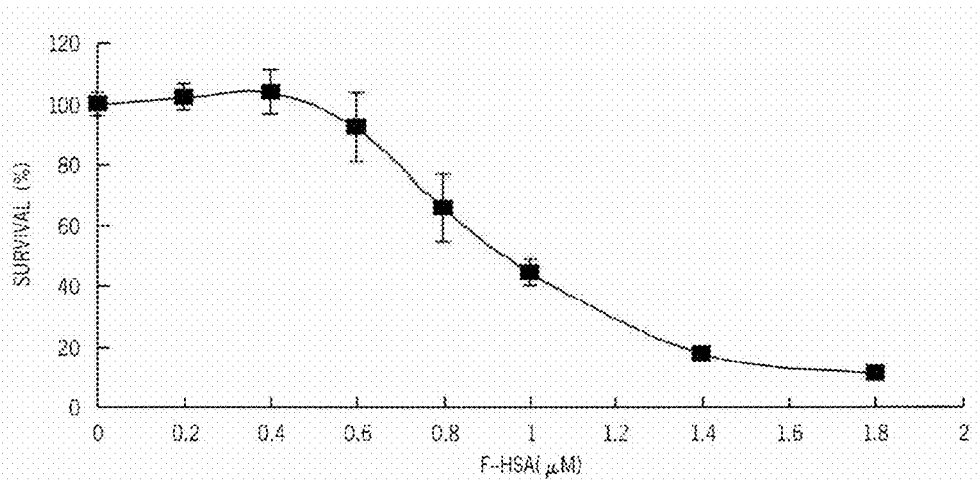
FIG. 16 is an implementation of experimental data showing the cytotoxic effects of F-HSA on cervical cancer cells.

FIG. 15 shows F-HSA's cytotoxic effect in SKOV-3 cells and FIG. 16 shows F-HSA's cytotoxic effect in CaSki cells. Each respective cell type was treated for 16 h in serum-free culture medium with various concentrations of F-HSA. Cell viability was determined by the MTT assay.

Example 9

F-HSA has a Cytotoxic Effect on Prostate Cancer Cells

Figure 17:
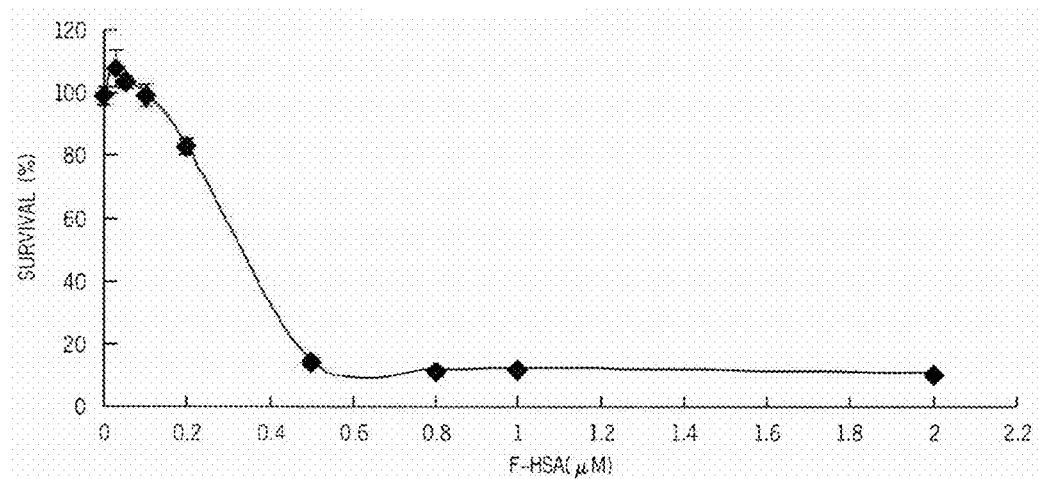
FIG. 17 is an implementation of experimental data showing the cytotoxic effects of F-HSA on prostate cancer cells.

FIG. 17 shows F-HSA's cytotoxic effect in PC-3 cells and FIG. 7 shows F-HSA's cytotoxic effect in 22 Rv1 cells. The respective cell type was treated for 16 h in serum-free culture medium with various concentrations of F-HSA. Cell viability was determined by the MTT assay.

Example 10

F-HSA has a Cytotoxic Effect on Lung Cancer Cell Lines

According to implementations shown in FIG. 19, F-HSA was shown to induce cytotoxicity in adenocarcinoma cell lines A549, CL1-0, Cl1-5, H1299, PC13, and PC14; squamous cell carcinoma lung cancer cell line H520; and large cell lung cancer carcinoma cell line H661. FIG. 19 shows the $IC_{50}$ of each of the respective cell lines.

Example 11

F-HSA Suppresses Tumor Cell Invasion and Migration In Vitro

Figure 20A:
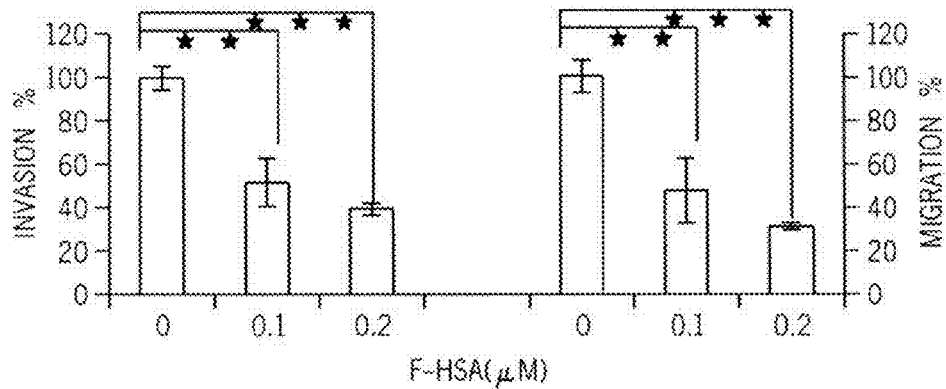
FIG. 20A-20H are implementations of experimental data showing the effect of F-HSA in reducing tumor cell migrations and invasion without effecting viability of normal cells.
Figure 20:
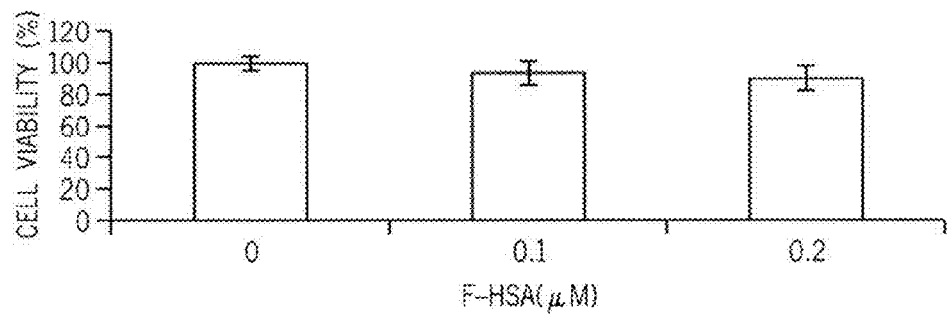
Figure 20:
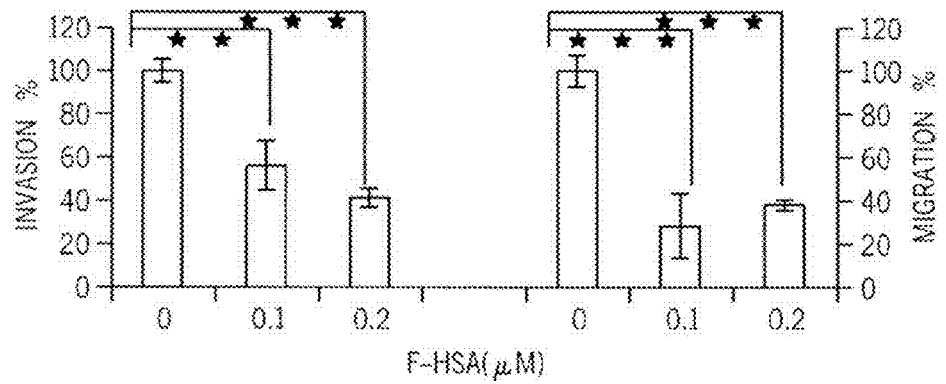
Figure 20D:
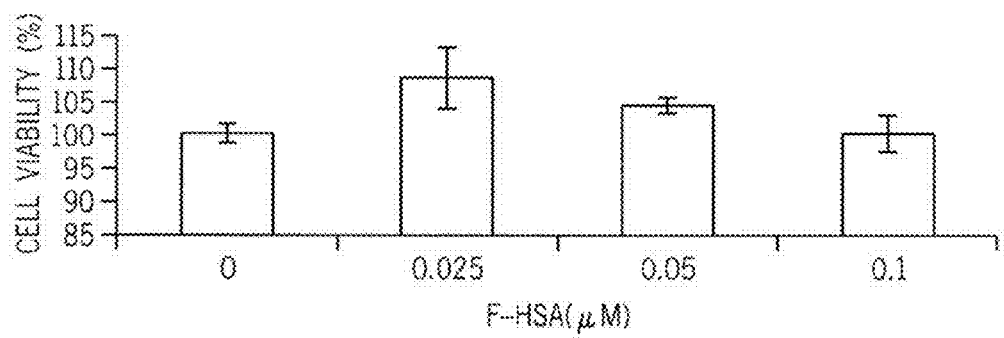
Figure 20E:
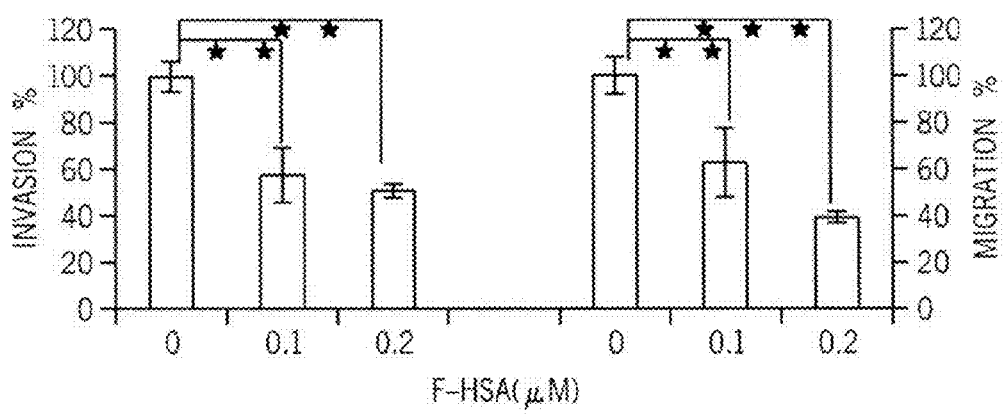
Figure 20F:
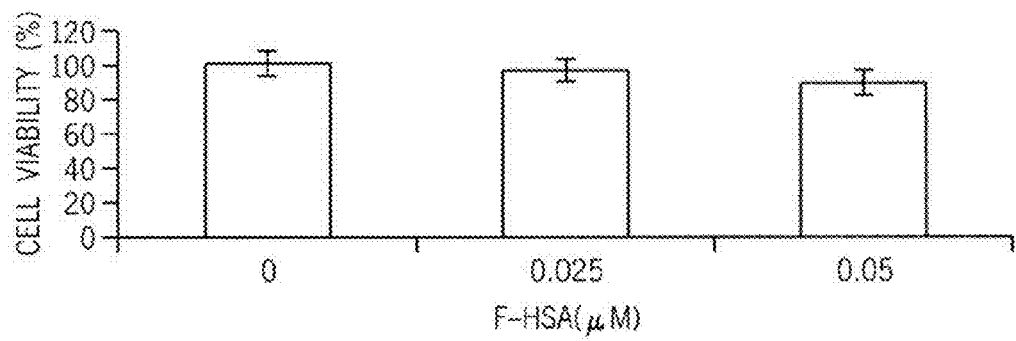
Figure 20G:
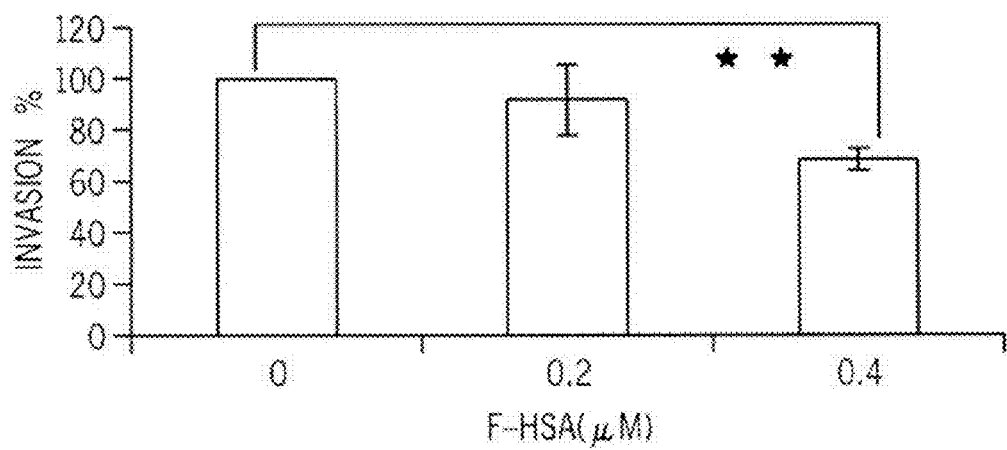
Figure 20H:
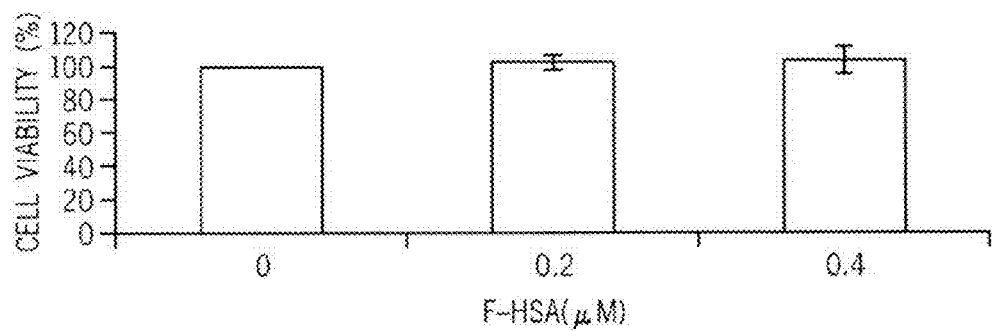

F-HSA was also shown to be effective in suppressing tumor cell invasion and migration in vitro, as shown according to implementations of experimental data in FIG. 20. As shown in FIGS. 9A, 9C, 9E, and 9G, F-HSA significantly reduced the tumor cells invasion/migration abilities, at concentrations which did not affect viability of either cancer or normal cells.

Example 12

F-HSA Suppressed Tumor Cell Metastasis In Vivo

Figure 21A:
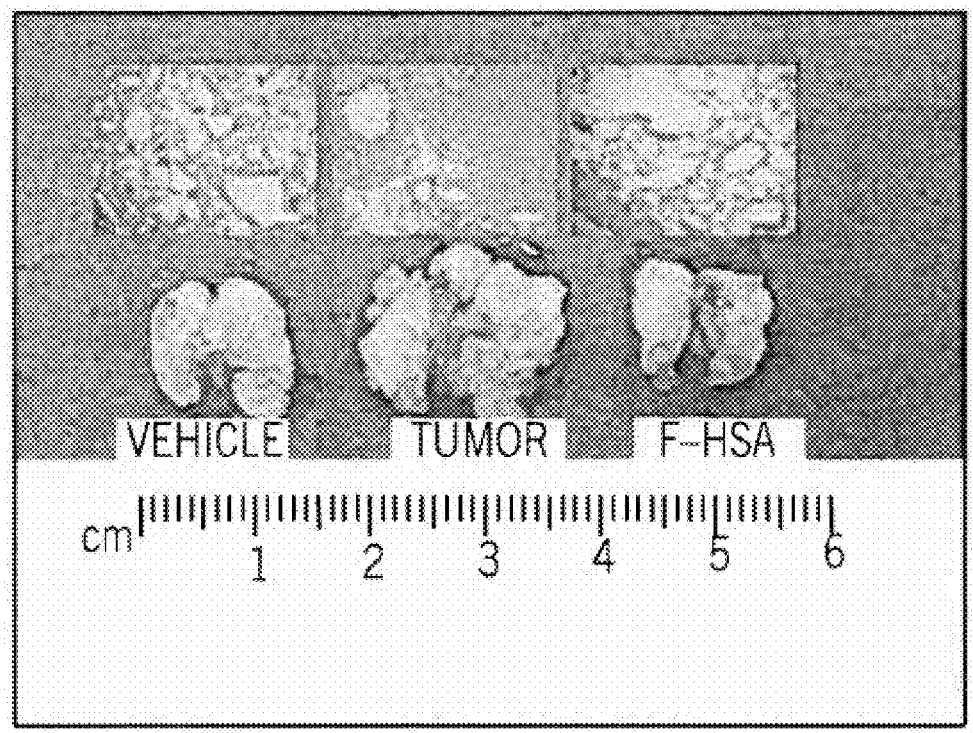
FIG. 21A-21C are implementations of experimental data showing the effect of F-HSA in suppressing the metastasis of mouse breast tumor TS/A cells to the lung.
Figure 21B:
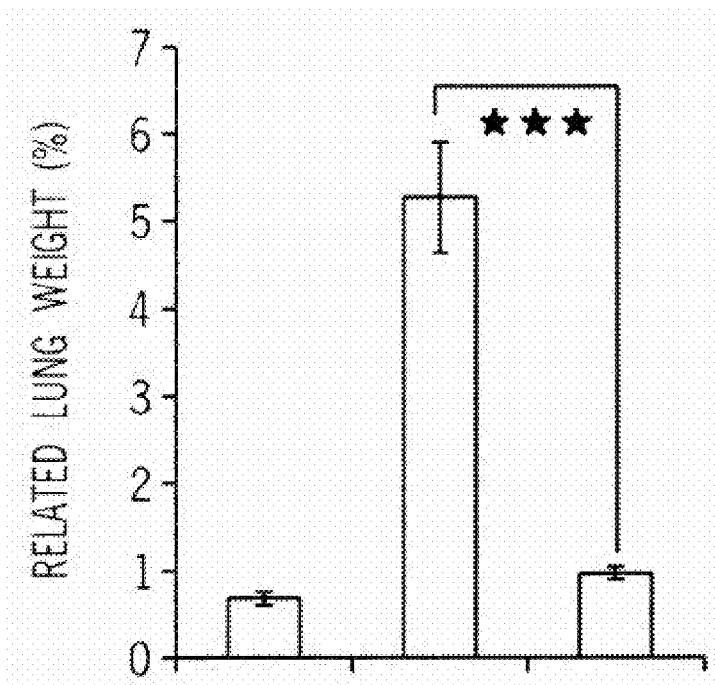
Figure 21C:
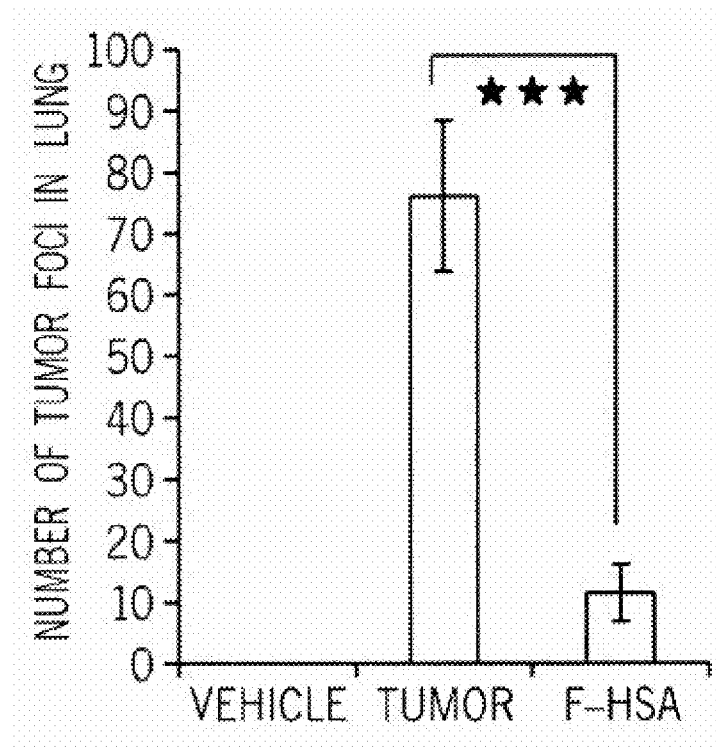
Figure 22A:
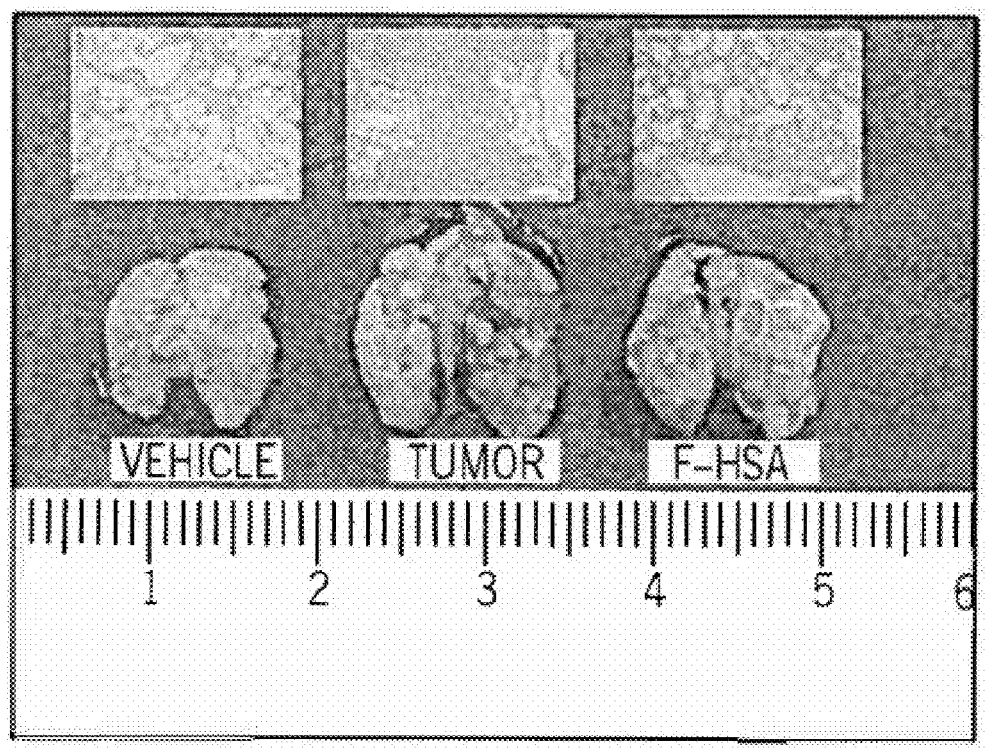
FIG. 22A-22C are implementations of experimental data showing the effect of F-HSA in suppressing the metastasis of mouse breast tumor MDA-MB-231 cells to the lung.
Figure 22B:
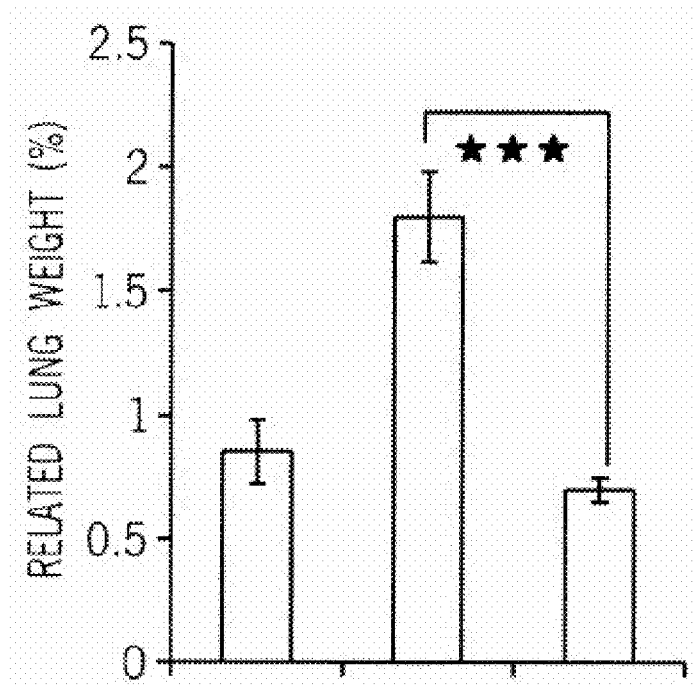
Figure 22C:
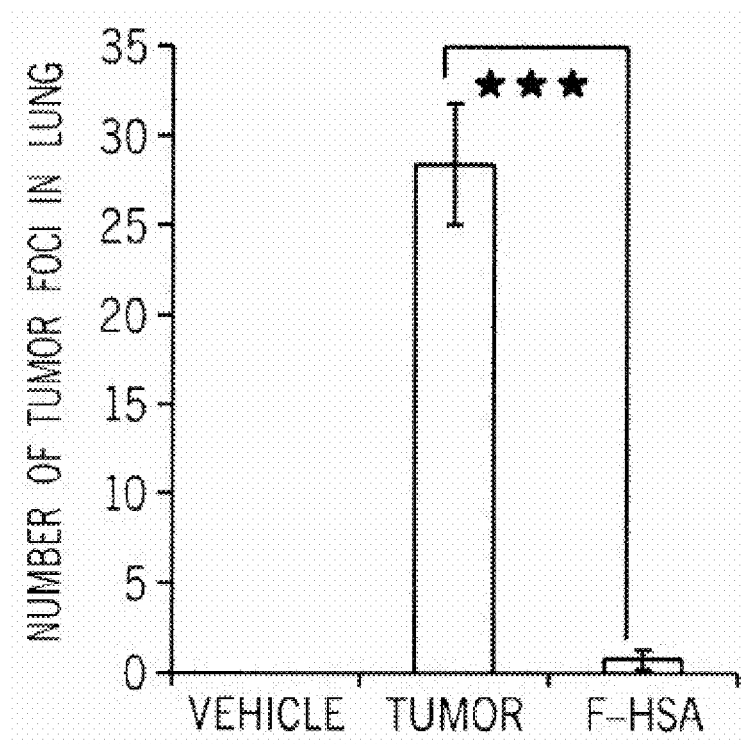

F-HSA suppressed breast cancer tumor cell lines TS/A and MDA-MB-231 in vivo. FIGS. 21A and 22A show F-HSA significantly suppressed the metastasis of breast cancer TS/A cells and MDA-MB-231 cells to lung compared with TS/A or MDA-MB-231 bearing mice without F-HSA treatment. FIGS. 21B, 21C, 22B, and 22C measure the weight and the number of tumor cell foci in the lung tissues, which further confirmed the efficacy of F-HSA in vivo.

According to implementations, breast cancer cells were injected via the tail vein of the subjects. Tumor cell foci detected in the lung tissue indicated that the breast cancer cells had metastasized into lung.

Materials and Methods

Preparation of F-HSA. Twenty milligrams of HSA was dissolved in 10 ml of PBS with 1% SDS (w/v). The HSA solution was sonicated for 5 min and subsequently applied to a Superdex-200, which was previously equilibrated with the eluting solution (25 mM Tris-HCl (pH 8.0), 1 mM EDTA, 0.1 M NaCl, and 0.05% SDS). The column was eluted at the rate of 1 ml/min and fractions C3 to C7 that contained HSA were pooled. The pooled fractions were concentrated to 2-3 mg/ml then dialyzed against PBS with Cellu-Sep T4/Nominal (MWCO: 12,000-14,000 Da) dialysis membrane. New PBS buffer was exchanged every two hours at room temperature three times. The yield of the HSA-5200 was about 75%.

Thioflavin T (ThT) fluorescence assay. Binding to ThT is one of the characteristics of amyloid-like proteins. For fluorescence measurements, increasing concentrations of proteins were incubated with 20 μM ThT for 1 h at room temperature, the fluorescence was then measured in triplicate on a Wallac Victor$^2$ 1420 Multilabel Counter (Perkin Elmer Life Science, Waltham, Mass., USA). Excitation and emission wavelengths were 430 nm and 486 nm, respectively. ThT background signal from buffer solution was subtracted from corresponding measurements.

Cell survival was determined by MTT colorimetric assay. Exponentially growing cells ($2 \times 10^4$ cells/well for TS/A) were seeded in a 96-well plate in medium with 10% FBS and incubated for 24 h. Treatment of cells with a series of concentrations of proteins was carried out in serum-free medium for 16 hr indication at 37° C. After treatment, MTT solution was added to each well (0.5 mg/ml), followed by a 4 h incubation period. The viable cell number is directly proportional to the production of formazan, which, following solubilization with isopropanol, can be measured spectrophotometrically at 570 nm by an ELISA plate reader.

Cell Viability Assays. Cell viability was measured by WST-1 assay according to the manufacturer's instructions (Roche, Mannheim, Germany). In brief, $2 \times 10^4$ cells were added to 100 μl media per well on a 96 well plate and incubated at 37° C. in 5% $CO_2$ overnight in a humidified incubator. The cells attached to the wells were incubated in serum-free medium and treated with various concentrations of F-HSA. After incubation at 37° C. in 5% $CO_2$ for 16 h to allow the drug to take effect, 10 μl WST-1 reagent was added to each well. The plate was then placed onto a shaking table and shaken at 150 rpm for 1 min. After incubation at 37° C. in 5% $CO_2$ for another 2 h to allow the WST-1 reagent to be metabolized, the proportion of surviving cells were determined by optical density (450 nm test wavelength, 690 nm reference wavelength). The percentage of surviving cells was calculated as (O.D. treatment/O.D. control)×100% while the percentage of growth inhibition was calculated as [1−(O.D. treatment/O.D. control)]×100%. According to this experiment, $IC_{50}$ is the concentration at which the reagent yields 50% inhibition of the cellular viability.

Cell Migration and Invasion Assays. Cell migration and invasion were determined by using Boyden chamber migration and invasion assay (Corning). In brief, the 8-μm pore membranes of the upper chambers were coated with 20 μg/ml fibronectin (for cell migration assay) or 40 μg/ml Matrigel (for cell invasion assay) and placed in a well with 1 ml of PBS and incubated for 2 h at 37° C. Cancer cells ($1 \times 10^5$) in 100 μl of serum free culture medium were seeded in the upper chamber for 1 h. A serially diluted concentration of F-HSA was added into the upper chamber and then the culture medium containing 10% FBS was added to the lower chamber. Cells were incubated for 24 h at 37° C. After incubation, cells on the upper side of the membrane were removed by wiping it with a cotton swab, and cells that had migrated onto the lower membrane surface were dissociated by using cell dissociation solution (Sigma) and counted by flow cytometer (BD company). At these concentrations, however, F-HSA did not affect cell viability when measured with the MTT assay, and as shown in FIGS. 9B, 9D, 9F, and 9H. Viability and cytotoxicity was measured using MTT or WST-1 assay. These kits are designed for the spectrophotometric measurement of cell growth as a function of mitochondrial activity in living cells (Roche).

Breast Cancer Cell Metastasis In Vivo. TS/A murine mammary adenocarcinoma cells were intravenously injected into the lateral tail vein of BALB/c mice or MDA-MB-231 human mammary adenocarcinoma cells were injected into nude mice. F-HSA (1 mg/kg) was then injected intravenously at next day and then one time every two days for ten times. At the end of F-HSA treatment, mice were sacrificed to detect the metastasis of lungs.

What is claimed is:

1. A method for suppressing human cancer metastasis comprising:
    administering to a human having a metastatic cancer an effective amount of fibrillar human serum albumin and a pharmaceutically acceptable carrier, wherein said administering reduces cancer metastasis in said human, and wherein said fibrillar human serum albumin is produced by a method comprising:
    dissolving human serum albumin in a detergent solution to provide dissolved human serum albumin;
    applying said dissolved human serum albumin through a gel filtration column with a pore size that can separate proteins of 70 kDa molecular weight and above;
    eluting said dissolved human serum albumin from said gel filtration column to provide an eluate; and
    removing said detergent from said eluate.

2. The method of claim 1, wherein said cancer is breast cancer.

3. The method of claim 1, wherein said cancer is prostate cancer.

4. The method of claim 1, wherein said cancer is ovarian cancer.

5. The method of claim 1, wherein said cancer is cervical cancer.

6. The method of claim 1, wherein said administering is selected from the group consisting of intravenous injection, subcutaneous injection, intraperitoneal injection, intraarterial injection, intramuscular injection, intralesional injection into the tumor, intralesional injection adjacent to the tumor, intravenous infusion, and intraarterial infusion.

7. The method of claim 1, wherein said administering is via slow release mode at or around tumor sites of said human subject.

8. The method of claim 1, wherein said administering comprises administering a second therapeutic agent.

9. The method of claim 8, wherein said second therapeutic agent is a chemotherapeutic agent.

10. The method of claim 8, wherein said second therapeutic agent is radiation therapy.

* * * * *